(12) United States Patent
Bovard et al.

(10) Patent No.: US 11,041,145 B2
(45) Date of Patent: Jun. 22, 2021

(54) CELL CULTURE

(71) Applicant: PHILIP MORRIS PRODUCTS S.A., Neuchatel (CH)

(72) Inventors: David Bovard, Erlach (CH); Karsta Luettich, Hauterive (CH)

(73) Assignee: Philip Morris Products S.A., Neuchatel (CH)

( * ) Notice: Subject to any disclaimer, the term of this patent is extended or adjusted under 35 U.S.C. 154(b) by 0 days.

(21) Appl. No.: 15/757,415

(22) PCT Filed: Aug. 17, 2017

(86) PCT No.: PCT/EP2017/070881
§ 371 (c)(1),
(2) Date: Mar. 5, 2018

(87) PCT Pub. No.: WO2018/036910
PCT Pub. Date: Mar. 1, 2018

(65) Prior Publication Data
US 2019/0119647 A1 Apr. 25, 2019

(30) Foreign Application Priority Data
Aug. 25, 2016 (EP) .................................. 16185725

(51) Int. Cl.
*C12N 5/071* (2010.01)
*C12M 3/00* (2006.01)
*G01N 33/50* (2006.01)

(52) U.S. Cl.
CPC ........... *C12N 5/0671* (2013.01); *C12M 21/08* (2013.01); *C12N 5/0688* (2013.01); *G01N 33/5014* (2013.01); *G01N 33/5082* (2013.01); C12N 2500/00 (2013.01); C12N 2502/14 (2013.01); C12N 2502/27 (2013.01)

(58) Field of Classification Search
CPC ................ C12N 5/0671; C12N 5/0688; C12N 2502/27; C12N 2500/00; C12N 2502/01; C12M 21/08; G01N 33/5082; G01N 33/5014
See application file for complete search history.

(56) References Cited

U.S. PATENT DOCUMENTS

| 5,985,542 | A | 11/1999 | Hirose |
| 7,052,720 | B1 | 5/2006 | Jones |
| 7,220,839 | B2 | 5/2007 | Mukaidani |
| 7,753,192 | B2 | 7/2010 | Mattos |
| 7,939,248 | B2 | 5/2011 | Silber |
| 8,530,237 | B2 | 9/2013 | Takahashi |
| 2008/0254535 | A1 | 10/2008 | Takahashi |
| 2014/0106356 | A1 | 4/2014 | Lee |
| 2014/0363473 | A1 | 12/2014 | Pollok |
| 2015/0276716 | A1 | 10/2015 | Kobayashi |
| 2017/0175078 | A1 | 6/2017 | Horikawa |

FOREIGN PATENT DOCUMENTS

| CN | 102559581 | 9/2014 |
| JP | 2013-102737 | 5/2013 |
| JP | 2016-054734 | 4/2016 |
| WO | WO 2009/013254 | 1/2009 |
| WO | WO 2010/042669 | 4/2010 |
| WO | WO 2012/123712 | 9/2012 |

OTHER PUBLICATIONS

Ma et al. Biochemical and Functional Changes of Rat Liver Spheroids During Spheroid Formation and Maintenance in Culture: I. Morphological Maturation and Kinetic Changes of Energy Metabolism, Albumin Synthesis, and Activities of Some Enzymes. Journal of Cellular Biochemistry (2003), 90, 1166-1175. (Year: 2003).*

Doostdar et al. The influence of culture medium composition on drug metabolising enzyme activities of the human liver derived Hep G2 cell line. FEBS Letters (1988), 241(1-2), 15-18. (Year: 1988).*

Keenan et al. Transforming Growth Factor-β Impairs Glucocorticoid Transactivation in Air-Liquid Interface Differentiated Primary Human Bronchial Epithelial Cells. Am J Respir Crit Care Med (2012), 189, A5684. (Year: 2012).*

Rebelo et al. Evaluation of the impact of matrix stiffness on encapsulated HepaRG spheroids. BMC Proceedings (2013), 7(Suppl. 6):p. 77, 2 pages. (Year: 2013).*

Leung et al. Investigation of the Barrier Properties of Differentiated Human Airway Epithelium from Normal and Asthmatics In Vitro. Am J Respir Crit Care Med (2012), 185, A4273. (Year: 2012).*

Liu et al. Three-dimensional spheroid cultures of A549 and HepG2 cells exhibit different lipopolysaccharide (LPS) receptor expression and LPS-induced cytokine response compared with monolayer. Innate Immunity (2011), 17(3), 245-255. (Year: 2011).*

Alépée, N. et al. (2014), "State-of-the-art of 3D cultures (organs-on-a-chip) in safety testing and pathophysiology" ALTEX 31, 441-477.

Alepee, Natalie, "State-of-the-Art of 3D Cultures (Organs-on-a-Chip) in Safety Testing and Pathophysiology", Alternatives to Animal Experimentation, ALTEX, Jan. 1, 2014.

Baxter et al., "Targeted Omics Analyses, and Metabolic Enzyme Activity Assays Demonstrate Maintenance of Key Mucociliary Characteristics in Long Term Cultures of Reconstituted Human Airway Epithelia", *Toxicoloy in Vitro* 29 (2015) 864-875.

Elaut, G. et al. (2006), "Molecular mechanisms underlying the dedifferentiation process of isolated hepatocytes and their cultures", *Curr. Drug Metab.* 7, 629-660.

http://bio.lonza.com/uploads/tx_mwaxmarketingmaterial/Lonza_ManualsProductInstructions_Clonetics_B-ALI_Air_Liquid_Interface_Medium_Instructions_for_Use.pdf.

Huch, Meritxell et al, "Modeling Mouse and Human Developmental Using Organoid Cultures", *Development (Cambridge)*, The Company of Biologists Ltd., United Kingdom, vol. 142, No. 18, Sep. 15, 2015, pp. 3113-3125.

(Continued)

*Primary Examiner* — Sean C. Barron
(74) *Attorney, Agent, or Firm* — Mueting Raasch Group

(57) ABSTRACT

There is described an isolated 3-dimensional liver spheroid wherein said spheroid has: increased ATP content as compared to a 3-dimensional liver spheroid cultured in Complete William's E medium alone; the same or increased activity of cytochrome P450 1A1 and cytochrome P450 1B1 as compared to a 3-dimensional liver spheroid cultured in Complete William's E medium alone; and increased albumin secretion as compared to a 3-dimensional liver spheroid cultured in William's E medium alone.

3 Claims, 10 Drawing Sheets

(56) References Cited

OTHER PUBLICATIONS

Iskandar AR et al., "Impact Assessment of Cigarette Smoke Exposure on Organotypic Bronchial Epithelial Tissue Cultures: A Comparison of Mono-Culture and Coculture Model Containing Fibroblasts", Toxicol Sci. Sep. 2015;147(1):207-21. doi: 10.1093/toxsci/kfv122.

Karp, P.H., et al. (2002), "An in vitro model of differentiated human airway epithelia. Methods for establishing primary cultures", Methods Mol. Biol. 188, 115-137.

Lee, Jin Woo et al., "Development of a 3D Cell Printed Construct Considering Angiogenesis for Liver Tissue Engineering,", Biofabrication, vol. 8, No. 1 15007, Jan. 12, 2016, pp. 1-13.

Li, A.P. (1997), "Primary hepatocyte cultures as an in vitro experimental model for the evaluation of pharmacokinetic drug-drug interactions", Adv. Pharmacol. 43, 103-130.

Li, Albert P., "The Use of Integrated Discrete Multiple Organ Co-culture (IdMOC) System for the Evaluation of Multiple Organ Toxicity", Atla. Alternatives to Laboratory Animals, London, GB, vol. 37, No. 4, Sep. 1, 2009, pp. 377-385.

Lübberstedt, et al. (2011), "HepaRG human hepatic cell line utility as a surrogate for primary human hepatocytes in drug metabolism assessment in vitro", J. Pharmacol. Toxicol. Methods 63, 59-68.

Maschmeyer I, et al, "Chip-based human liver-intestine and liver-skin co-cultures—A first step toward systemic repeated dose substance testing in vitro", Eur J Pharm Biopharm. Sep. 2015;95(Pt A):77-87. doi: 10.1016/j.ejpb.2015.03.002. Epub Apr. 6, 2015.

Maschmeyer I, et al., "A four-organ-chip for interconnected long-term co-culture of human intestine, liver, skin and kidney equivalents", Lab Chip. Jun. 21, 2015;15(12):2688-99. doi: 10.1039/c5lc00392j.

Materne EM, et al., "A multi-organ chip co-culture of neurospheres and liver equivalents for long-term substance testing", J Biotechnol. Jul. 10, 2015;205:36-46. doi: 10.1016/j.jbiotec.2015.02.002. Epub Feb. 9, 2015.

Materne, E.-M., et al.. (2015). "The Multi-organ Chip—A Microfluidic Platform for Long-term Multi-tissue Coculture", J. Vis. Exp.

Mathis et al., "Human Bronchial Epithelial Cells Exposed in Vitro to Cigarette Smoke at the Air-Liquid Interface Resemble Bronchial Epithelium From Smokers", Am J. Physiol Lung Cell Mol Physiol 304: L489-L503, 2013.

Poon, Christine et al., "A dynamic Perfusion Bioreactor Approach for Engineering Respiratory Tissues In-Vitro, The Effect of Applied Compressive Loading on Tissue-Engineered Cartilage Constructs Cultured with TGF-BETA3", IEEE, Jul. 3, 2013, pp. 6224-6227.

Prytherch ZC, BéruBé KA, "A normal and biotransforming model of the human bronchial epithelium for the toxicity testing of aerosols and solubilised substance", Altern Lab Anim. Dec. 2014;42(6):377-81.

Ravi, M., Paramesh, V., Kaviya, S.R., Anuradha, E., and Solomon, F.D.P. (2015). "3D cell culture systems: advantages and applications", J. Cell. Physiol. 230, 16-26.

Szabo, M., et al. "Comparison of human hepatoma HepaRG cells with human and rat hepatocytes in uptake transport assays in order to predict a risk of drug induced hepatotoxicity", PloS One 8, e59432.

Takahashi, Y., Hori, Y., Yamamoto, T., Urashima, T., Ohara, Y., and Tanaka, H. (2015), "3D spheroid cultures improve the metabolic gene expression profiles of HepaRG Cells", Biosci. Rep. 35.

Tong, J.Z., et al., "Long-Term Culture of Adult Rat Helpatocyte Spheroids", Experimental Cell Research, Elsevier, Amsterdam, NL, vol. 200, No. 2, Jun. 1, 1992, pp. 326-332.

Wagner I, et al., "A dynamic multi-organ-chip for long-term cultivation and substance testing proven by 3D human liver and skin tissue co-culture," Lab on a Chip. Sep. 21, 2013;13(18):3538-47. doi: 10.1039/c3lc50234a.

European Search Report for Application No. 16185725.5-1402 dated Mar. 22, 2017 (21 pages).

PCT Search Report and Written Opinion for PCT/EP2017/070881 dated Dec. 22, 2017 (17 pages).

Summons to Oral Proceedings for European Application No. 16185725.5 dated May 13, 2020 (9 pages).

D9—Thermo Fisher Scientific GlutaMAX™ product page with FAQs on the difference between GlutaMAX™ and CTS-GlutaMAX™-1.

D10—Thermo Fisher Scientific DMEM spreadsheet and catalogue numbers.

D11—Acquisition of Life Technologies by Thermo Fisher Scientific FAQs.

D12—Lonza FAQs on the difference between EBM™ and EMB™-2.

D13—Lonza FAQs on the difference between SkBM™ and SKBM™-2.

D14—Lonza FAQs on the difference between KGM™, KGM™-2, and KGM™-Gold.

D15—Lonza FAQs on the difference between EGM™, EGM™-2, EGM™-MV and EGM™-2MV.

D16—Lonza BrainPhys™ Neuronal medium product information.

D17—Lonza BrainPhys™ without Phenol Red Medium Product Information.

D18—STEMCELL Technologies webpage for STEMdiff™ APEL™-2.

D19—STEMCELL Technologies webpage for STEMdiff™ APEL™2-LI.

D20—STEMCELL Technologies webpage showing product Pneumacult®-ALI and PneumaCult®ALI-S.

D21—STEMCELL Technologies manual for mTeSR Plus.

D22—Rebranding announcement for STEMCELL Technologies.

D23—PneumaCult®-ALI kit information sheet.

D24—Complete B-ALI media BulletKit Instruction manual.

D25—HepaRG User Guide.

Office Action issued in Japan for Application No. 2018-519751 dated Sep. 2, 2019 (6 pages). English translation included.

* cited by examiner

Week 1

Week 2

Week 3

Week 4

CELL CULTURE

This application is a U.S. National Stage Application of International Application No. PCT/EP2017/070881 filed Aug. 17, 2017, which was published in English on Mar. 1, 2018, as International Publication No. WO 2018/036910 A1. International Application No. PCT/EP2017/070881 claims priority to European Application No. 16185725.5 filed Aug. 25, 2016.

FIELD OF THE INVENTION

The present invention relates to the field of cell culture, in particular, to the culture of 3-dimensional cells, 3-dimensional co-cultures and methods and uses thereof.

BACKGROUND

Toxicological studies using 2-dimensional cell culture systems have been used to examine the effects of drugs on cell survival and enzyme activity etc. While being able to grow cells in flat layers on plastic surfaces is straight forward and permits the study of several aspects of the cellular physiology and responses to stimuli, they do not reflect the real structure and architecture of an organ. In 2-dimensional monolayers, the extracellular matrix, the cell-to-cell and cell-to-matrix interactions, which are essential for the differentiation, proliferation and cellular functions are lost.

3-dimensional culture systems can form a functional tissue with similar features to those observed in vivo. As compared to the 2-dimensional culture systems, 3-dimensional cell culture allows cells to interact with their surroundings in all three dimensions and are more physiologically relevant. Such cells can show improvements in viability, proliferation, differentiation, morphology, response to stimuli, drug metabolism, gene expression and protein synthesis and the like. 3-dimensional cell culture can produce specific tissue-like structures and mimic functions and responses of real tissues in a manner that is more physiologically relevant than traditional 2-dimensional cell monolayers.

Several 3-dimensional tissues mimicking human organs are commercially available. Lung 3-dimensional organotypic tissues for example can be prepared using primary human cells grown at the air-liquid interface (ALI) where these cells will differentiate and form a functional tissue. These 3-dimensional tissues bear close morphological resemblance and metabolic characteristics to human bronchial tissues. They are composed of basal, goblet and ciliated cells arranged in a pseudostratified structure. Similar to the lung, actively beating cilia are present allowing the study of their function and activity. Similar levels of xenobiotic enzyme-encoding mRNA have been found in these 3-dimensional ALI cultures compared with human lungs. In addition, these tissues can be maintained in vitro for an extended period of time. This 3-dimensional model of lung tissue is an appropriate model to explore the effects of aerosols and drugs etc., and also to observe the effect of repeated exposure.

Other 3-dimensional models have also been described, including 3-dimensional liver spheroid models. Liver spheroids can be composed of several cell types that were initially used in 2-dimensional cultures to determine the effects of drug treatments on liver cells. However, primary human hepatocytes do not express metabolic enzymes for more than 5 days, despite having similar phase 1 metabolic gene expression compared with human liver tissues. Another limitation is the short viability that makes repeated dosing difficult. These drawbacks can be overcome by the use of alternative, long-lived liver cell lines such as HepaRG cells (ThermoFisher Scientific). HepaRG cells are a human hepatic progenitor cell line that retain many characteristics of primary human hepatocytes. They have a greater liver-specific and phase 1 metabolic gene expression compared to primary hepatocytes. In addition, their lifespan is strongly increased. Formation of HepaRG cells in 3-dimensional spheroids increases lifespan and metabolic capabilities.

The interest in liver-dependent toxicological studies pertains to the ability of this tissue to metabolize several compounds by xenobiotic metabolism. While many chemical compounds are inactivated and solubilized, some are bio-activated and therefore become toxic. As a consequence, studying the toxicity of a compound in an organ without taking into account the bio-activation process taking place in the liver might lead to underestimated toxic effects of the tested substances. Hence, in the field of aerosol exposure, there is a need for an improved approach to study the penetration of a substance in the lung and its further bio-activation in the liver. The present invention seeks to address this need in the art.

SUMMARY

In the present disclosure, individual lung and liver cultures have been established and characterised morphologically and functionally. In order to facilitate the co-culture of both cell types, cell culture conditions and specifically cell culture media have been identified so that both lung and liver cultures maintain viability, structural integrity and functional capabilities. Advantageously, this makes it possible to develop a multiple organ system that recreates the interaction between the lung and the liver and, significantly, without the loss of each of the cells individual characteristics. The finding herein that lung epithelial cell culture medium can be used to successfully grow and maintain liver spheroids and can even significantly improve the characteristics of the liver spheroids was wholly unexpected. Using this multiple organ system will greatly assist in understanding the role of the liver on the metabolism of lung-absorbed compounds—such as aerosols. The present disclosure provide a valuable tool to study the impact of compounds in a 3-dimensional, cell culture system that is closer, and thus is expected to be more predictive, of the clinical situation and offer a unique, simple and inexpensive 3-dimensional liver and lung cell co-culture system.

ASPECTS AND EMBODIMENTS OF THE PRESENT INVENTION

In a first aspect, there is provided an isolated 3-dimensional liver spheroid, wherein the spheroid has: increased ATP content as compared to a 3-dimensional liver spheroid cultured in Complete William's E medium alone; the same or increased activity of cytochrome P450 1A1 and cytochrome P450 1B1 as compared to a 3-dimensional liver spheroid cultured in Complete William's E medium alone; and increased albumin secretion as compared to a 3-dimensional liver spheroid cultured in William's E medium alone.

The term "Complete William's E medium alone" means a culture medium consisting of Complete William's E medium only, that is a culture medium consisting of 100% (v/v) Complete William's E medium.

In another aspect, there is provided an isolated 3-dimensional liver spheroid for use in a 3-dimensional multi-organ culture system obtained or obtainable by a process comprising: culturing a 3-dimensional liver spheroid in a cell culture medium comprising or consisting or consisting essentially of either: (a) Complete PneumaCult-ALI medium; or (b) Complete B-ALI medium; or (c) Complete PneumaCult-ALI medium and Complete William's E medium, or (d) Complete B-ALI medium and Complete William's E medium, for a period of time that is sufficient to obtain a 3-dimensional liver spheroid in which: ATP content is increased as compared to a 3-dimensional liver spheroid cultured in Complete William's E medium alone; cytochrome P450 1A1 and cytochrome P450 1B1 activity is the same or increased as compared to a 3-dimensional liver spheroid cultured in Complete William's E medium alone; and albumin secretion is increased as compared to a 3-dimensional liver spheroid cultured in Complete William's E medium alone.

Suitably, the spheroid is or is derived from a human hepatic progenitor cell line, suitably, wherein the spheroid is or is derived from a HepaRG cell.

Suitably, the spheroid is cultured in a cell culture medium comprising or consisting or consisting essentially of either: (a) Complete PneumaCult-ALI medium; or (b) Complete B-ALI medium; (c) Complete PneumaCult-ALI medium and Complete William's E medium, or (d) Complete B-ALI medium and Complete William's E medium.

In a further aspect, there is provided a co-culture comprising the 3-dimensional liver spheroid according to any of the preceding claims and a 3-dimensional lung epithelial cell.

Suitably, the co-culture is maintained in a cell culture medium comprising or consisting or consisting essentially of either: (a) Complete PneumaCult-ALI medium; or (b) Complete B-ALI medium; or (c) Complete PneumaCult-ALI medium and Complete William's E medium, or (d) Complete B-ALI medium and Complete William's E medium. In a further aspect, there is provided 3-dimensional organ culture system comprising the isolated 3-dimensional liver spheroid described herein.

In a further aspect, there is provided a 3-dimensional multi-organ culture system comprising the isolated 3-dimensional liver spheroid as described herein and further comprising at least one other 3-dimensional cell type, or comprising the co-culture described herein.

Suitably, the 3-dimensional liver spheroid is submerged in culture medium contained on the culture system.

Suitably, the 3-dimensional multi-organ culture system further comprises a 3-dimensional lung epithelial cell, suitably, wherein the 3-dimensional lung epithelial cell is at an air liquid interface on the 3-dimensional multi-organ culture system.

In a further aspect, there is provided a 3-dimensional multi-organ culture system comprising: (a) a first organ growth section comprising a first organ cavity adapted to submerge a first 3-dimensional cell type in a culture medium; (b) a second organ growth section comprising a second organ cavity adapted to culture a second 3-dimensional cell type at an air liquid interface, the second 3-dimensional cell type being a cell type that is different than the first 3-dimensional cell type; and (c) a culture medium reservoir connecting the first organ cavity and the second organ cavity to allow for the flow of culture medium there between.

Suitably, the first organ cavity and second organ cavity contain the same culture medium.

Suitably, the 3-dimensional multi-organ culture system comprises the co-culture described herein.

Suitably, the 3-dimensional organ culture system or the 3-dimensional multi-organ culture system is miniaturised.

Suitably, the 3-dimensional organ culture system or the 3-dimensional multi-organ culture system comprises or is a microfluidic device, suitably, wherein said system is an organ-on-a-chip.

In a further aspect, there is provided a cell culture medium comprising or consisting or consisting essentially of: (a) a mixture of Complete PneumaCult-ALI medium and Complete William's E medium; or (b) a mixture of Complete B-ALI medium and Complete William's E medium.

Suitably, the cell culture medium further comprises the 3-dimensional liver spheroid or the co-culture described herein.

In a further aspect, there is provided a 3-dimensional multi-organ culture system comprising a culture medium, said culture medium selected from the group consisting of a culture medium comprising or consisting or consisting essentially of either: (a) Complete PneumaCult-ALI medium; or (b) Complete B-ALI medium; or (c) Complete PneumaCult-ALI medium and Complete William's E medium, or (d) Complete B-ALI medium and Complete William's E medium or a combination of two or more thereof.

In a further aspect, there is provided a method of preparing a 3-dimensional liver spheroid for use in a 3-dimensional organ culture system comprising: (i) providing a 3-dimensional liver spheroid; (ii) contacting the 3-dimensional liver spheroid with a culture medium comprising or consisting or consisting essentially of either: (a) Complete PneumaCult-ALI medium; or (b) Complete B-ALI medium; or (c) Complete PneumaCult-ALI medium and Complete William's E medium, or (d) Complete B-ALI medium and Complete William's E medium; and (iii) obtaining a 3-dimensional liver spheroid for use in a 3-dimensional organ culture system.

In a further aspect, there is provided a method of preparing a co-culture comprising or consisting or consisting essentially of a 3-dimensional liver spheroid and a 3-dimensional lung epithelial cell for use in a 3-dimensional multi-organ culture system comprising: (i) providing a 3-dimensional liver spheroid and a 3-dimensional lung epithelial cell; (ii) contacting the 3-dimensional liver spheroid and the 3-dimensional lung epithelial cell with a culture medium comprising or consisting or consisting essentially of either: (a) Complete PneumaCult-ALI medium; or (b) Complete B-ALI medium; or (c) Complete PneumaCult-ALI medium and Complete William's E medium, or (d) Complete B-ALI medium and Complete William's E medium; and (iii) obtaining a co-culture of a 3-dimensional liver spheroid and a 3-dimensional lung epithelial cell.

In a further aspect, there is provided an in vitro method for assessing the response of a 3-dimensional liver spheroid to an agent, the method comprising: (i) contacting the 3-dimensional liver spheroid or the co-culture or the 3-dimensional organ culture system, or the 3-dimensional multi-organ culture system as described herein with at least one agent; and (ii) measuring one or more responses of the 3-dimensional liver spheroid or the co-culture or the 3-dimensional organ culture system or the 3-dimensional multi-organ culture system after contact with the at least one agent; wherein a difference in the one or more responses before and after contact with the at least one agent is indicative that the agent modulates the response of the cell.

In a further aspect, there is provided an in vitro method for assessing the response of a 3-dimensional liver spheroid and a 3-dimensional lung epithelial cell to an agent, the method comprising: (i) contacting the co-culture or the 3-dimensional organ culture system or the 3-dimensional multi-organ culture system with at least one agent; and (ii) measuring one or more responses of the co-culture or the 3-dimensional organ culture system or the 3-dimensional multi-organ culture system after contact with the at least one agent; wherein a difference in the one or more responses before and after contact with the at least one agent is indicative that the agent modulates the response of the cell.

Suitably, step (ii) comprises measuring the penetration of the at least one agent into the 3-dimensional lung epithelial cell.

Suitably, the in vitro method comprises the further step of: (iii) measuring the bio-activation of the at least one agent in the 3-dimensional liver spheroid; wherein the measurements in steps (ii) and (iii) are carried out simultaneously or wherein the measurement in step (iii) is carried out after the measurement in step (ii).

Suitably, the agent is an aerosol, more suitably, the aerosol is or is derived from smoke, suitably, cigarette smoke.

In a further aspect, there is provided the use of a cell culture medium comprising or consisting or consisting essentially of either: (a) Complete PneumaCult-ALI medium; or (b) Complete B-ALI medium; or (c) Complete PneumaCult-ALI medium and Complete William's E medium, or (d) Complete B-ALI medium and Complete William's E medium, for culturing a 3-dimensional liver spheroid or a 3-dimensional lung epithelial cell or for co-culturing a 3-dimensional liver spheroid and a 3-dimensional lung epithelial cell.

In a further aspect, there is provided the use of the 3-dimensional organ culture system or the 3-dimensional multi-organ culture system as described herein for toxicity testing or for drug discovery or for determining the penetration of an agent into lung cells and/or for determining the bio-activation of an agent in liver cells, suitably, wherein the agent is an aerosol.

A further aspect relates to a liver spheroid, a co-culture, a 3-dimensional organ culture system, a 3-dimensional multi-organ culture system, a cell culture medium, a method or a use substantially as described herein and with reference to the accompanying description and drawings.

Further particular and preferred aspects are set out in the accompanying independent and dependent claims. Features of the dependent claims may be combined with features of the independent claims as appropriate, and in combinations other than those explicitly set out in the claims. Combinations of one or more of the embodiments set forth above are therefore also disclosed.

DETAILED DESCRIPTION

Figure 1:
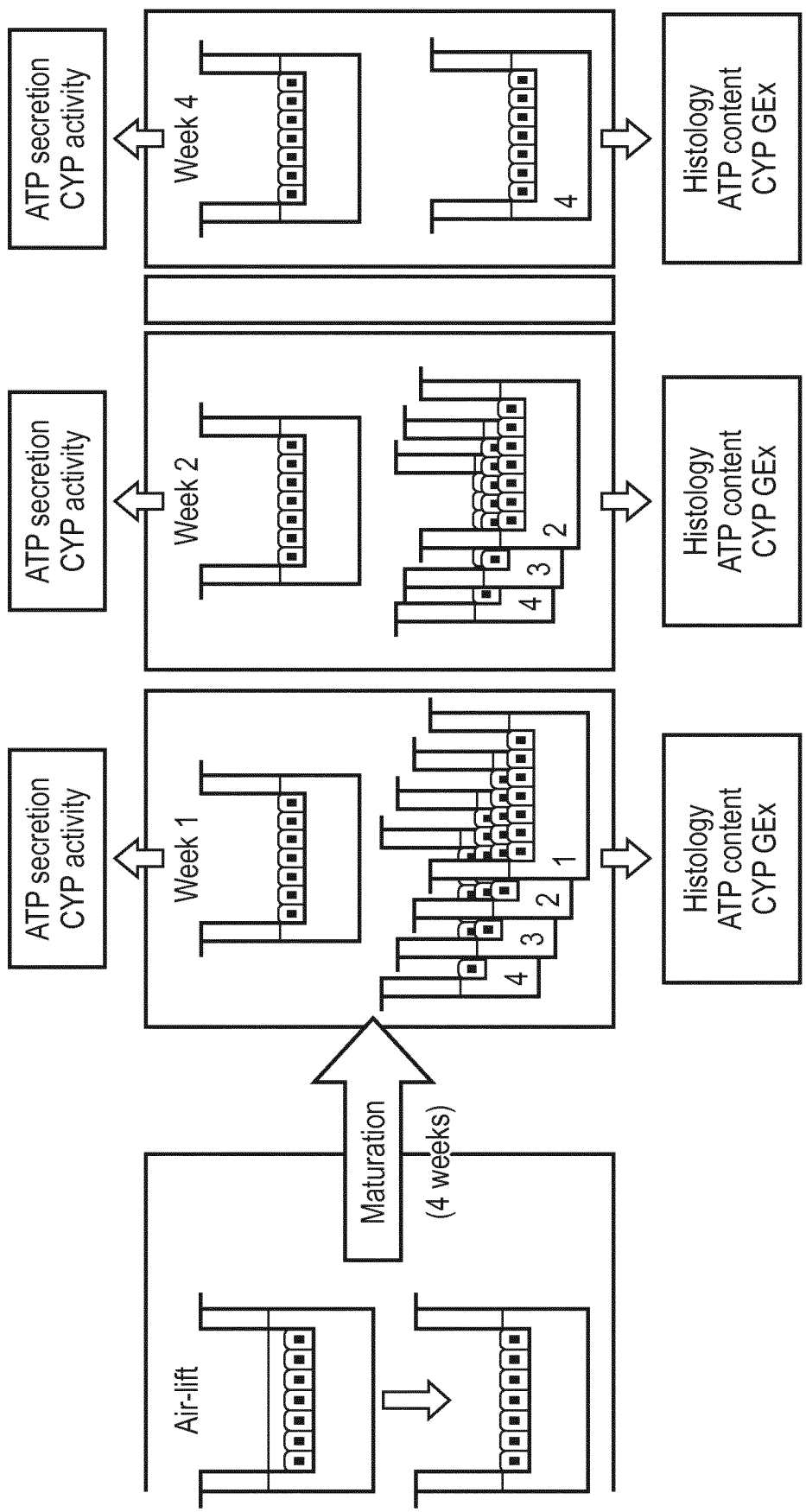
FIG. 1. Schematic overview of experimental design and endpoints for the characterisation of 3-dimensional organotypic lung tissues (GEx: Gene expression).
Figure 2:
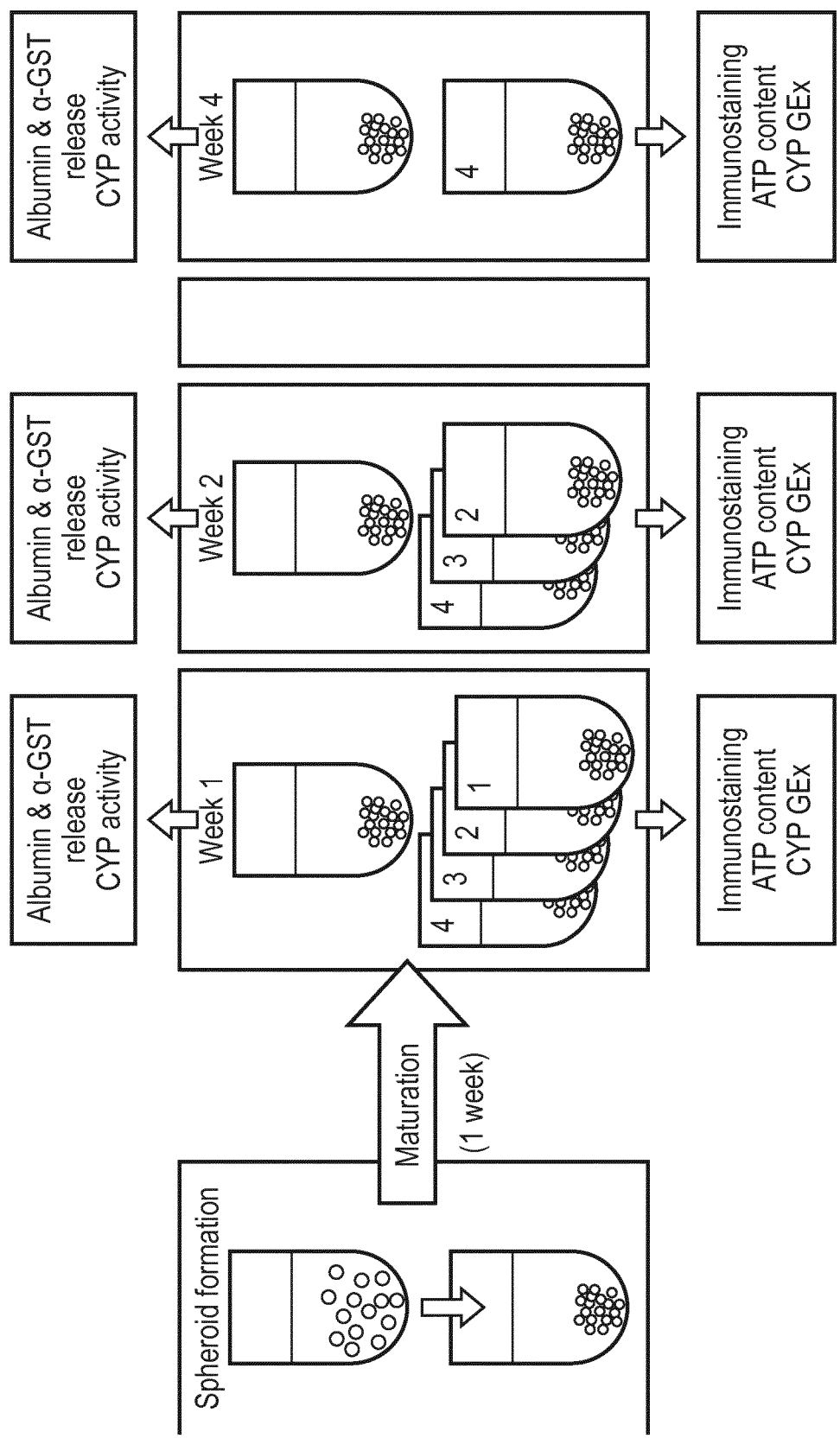
FIG. 2. Schematic overview of experimental design and endpoints for the characterization of liver spheroids (GEx: Gene expression).
Figure 3:
FIG. 3. Hematoxylin & eosin and Alcian blue staining of 3-dimensional organotypic lung cultures at 1, 2, 3, and 4 weeks following maturation. Representative cross-sections of epithelium are shown at 20× magnification.
Figure 3:
Figure 3:
Figure 3:
Figure 4:
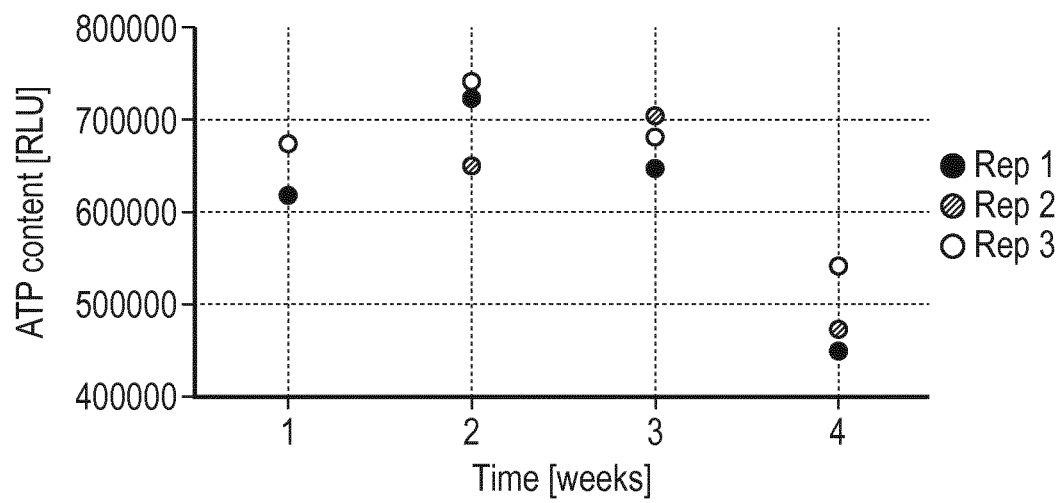
FIG. 4. ATP content of 3-dimensional organotypic lung cultures is measured at 1, 2, 3, and 4 weeks following maturation. Results for 3 independent measurements are shown. Rep: Replicate; RLU: Relative light unit FIG. 5. ATP secretion into the apical surface liquid of 3-dimensional organotypic lung cultures is measured in response to stimulation with hypotonic saline at 1, 2, 3, and 4 weeks following maturation. Results for 6 independent measurements are shown. Rep: Replicate FIG. 6. Cytochrome P450 1A1/B1 activity is measured in 3-dimensional organotypic lung cultures at 1, 2, 3, and 4 weeks following maturation. Results show basal CYP activity, induced activity following 48-h treatment with TCDD and rifampicin, and induced activity following inhibition with α-naphtoflavone. Results are presented as mean±SEM of 3 independent experiments. The dotted line indicates the trend based on the average value per time point.
Figure 5:
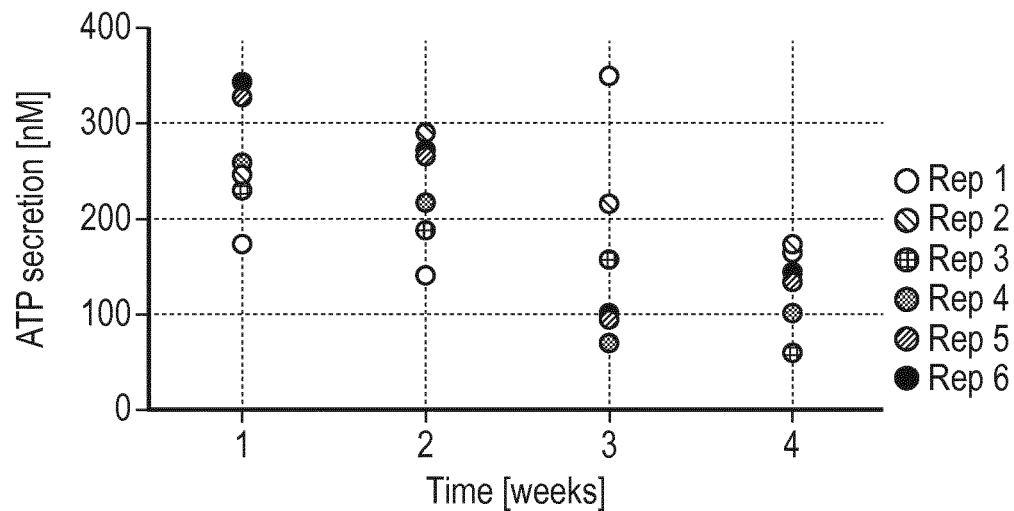
Figure 6:
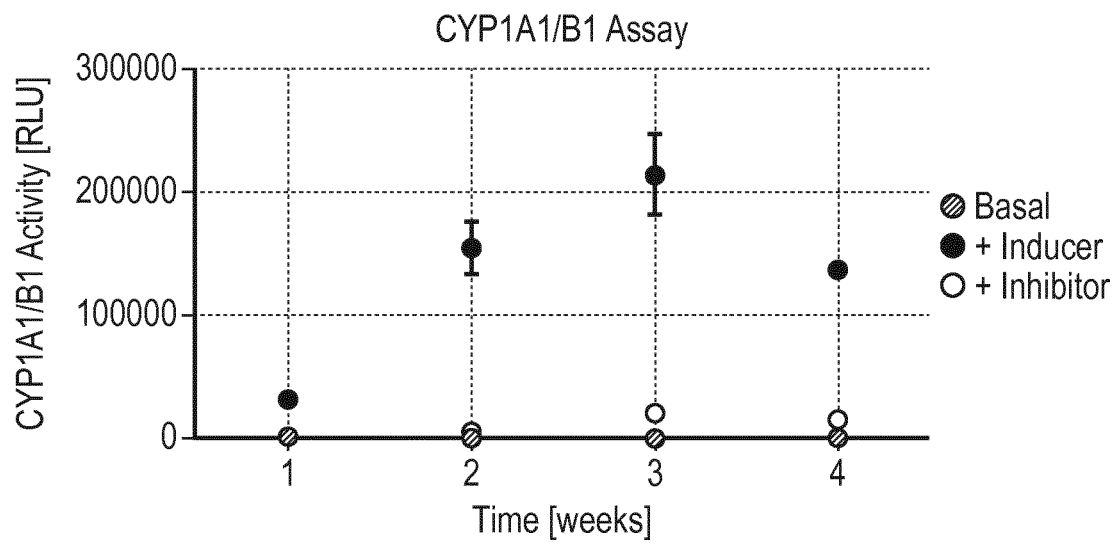

The practice of the present disclosure employs, unless otherwise indicated, conventional techniques of molecular biology, microbiology, cell biology and biochemistry. Such techniques are explained fully in the literature, such as, in Molecular Cloning: A Laboratory Manual, second edition (Sambrook et al., 1989) Cold Spring Harbor Press; Oligonucleotide Synthesis (M J. Gait, ed., 1984); Methods in Molecular Biology, Humana Press; Cell Biology: A Laboratory Notebook (J. E. CelMs, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, I B. Griffiths, and D. G. Newell, eds., 1993-8) J. Wiley and Sons; Methods in Enzymology (Academic Press, Inc.); Current Protocols in Molecular Biology (F. M. Ausubel et al., eds., 1987); PCR: The Polymerase Chain Reaction, (Mullis et al., eds., 1994). Procedures employing commercially available kits and reagents will typically be used according to manufacturer-defined protocols unless otherwise indicated.

The technical terms and expressions used herein are generally to be given the meaning commonly applied to them in the pertinent art of molecular biology, microbiology, cell biology and biochemistry. All of the following term definitions apply to the complete content of this application.

The term "comprising" does not exclude other elements or steps.

The term "consisting essentially of" refers to those elements required for a given embodiment. The term permits the presence of elements that do not materially affect the basic and novel or functional characteristic(s) of that embodiment. The term allows the presence of other components or ingredients in addition to the components or ingredients recited, provided that the essential characteristics of the composition are not materially affected by their presence. In the context of a cell culture medium, the term permits the presence of elements or ingredients that do not materially affect the basic and novel or functional characteristic(s) of the cell culture medium. The term allows the presence of other elements or ingredients in addition to the elements or ingredients recited, provided that the essential characteristics of the cell culture medium are not materially affected by their presence. For example, the term allows the presence of other elements or ingredients in addition to the elements or ingredients recited, provided that the essential characteristics of cells cultured in the cell culture medium are not materially affected by their presence as compared to cells cultured in a cell culture medium that does not include the other elements or ingredients.

The indefinite article "a" or "an" does not exclude a plurality.

Cell Culture

Cell culture generally refers to the removal of cells from a tissue prior to growth in an artificial environment. The cells to be cultured can be removed directly from a tissue containing the cell to be cultured and optionally treated with enzymatic or mechanical means prior to culture. As an alternative, the cells to be cultured can be derived from a prior established strain or line of cell. Cell culture can provide a system for studying various aspects of a cell including the physiology; the biochemistry; the effects of drugs or compounds, including aerosols; the screening and development or optimisation of drugs or compounds; the study of drug or compound efficacy; the study of drug or compound absorption; toxicity screenings; toxicology; target discovery; pharmacokinetics; pharmacodynamics; and regenerative medicine.

Cells grow in an artificial environment containing a cell culture medium that supplies growth factors, hormones, gases and essential nutrients—such as vitamins, amino acids, carbohydrates, minerals and the like, and in which the artificial environment is regulated, for example, in terms of temperature, pH and pressure. Some cells require anchorage to a solid or semi-solid substrate while other cells can grow whilst floating in a culture medium.

The present disclosure includes the use of "3-dimensional cell culture", which includes any method that provides for the culture of a cell in 3 dimensions, with or without the use of a matrix or scaffold. A number of different 3-dimensional cell culture methods have been developed including, spheroid cultures and organotypic cultures. Spheroid systems, especially liver spheroid systems, are of particular interest in the present disclosure.

Spheroids

The term "spheroid" assumes the meaning as normally understood in the art which is either a single cell that divides into a ball of cells in 3-dimensions, or an aggregation of multiple cells in 3-dimensions, either with or without the use of a matrix or scaffold to support in 3-dimensional cell growth within the spheroid. The 3-dimensional spheroid can be an adherent spheroid or a spheroid grown in suspension.

Several different systems for culturing spheroids are available, including spheroids grown as aggregates, for example, on nanoculture plates, in suspension culture, on gels, on plastic coated with poly-HEMA, via cell encapsulation or as aggregates via a hanging droplet system. Other methods include the use of spinner flasks, rotation systems, concave plate methods and liquid-overlay. Bioreactors can also be adapted for use in 3-dimensional spheroid cell culture. In one embodiment, the method used is the hanging droplet system—such as the GravityPLUS Hanging Drop System (InSphero). This method involves the use of the GravityTRAP ULA Plate which is a non-adhesive coated microtiter plate designed for the production of spheroids. Spheroid maturation typically occurs within 2 to 5 days of seeding depending on the cell type and culture conditions. Suitably, the spheroids are cultured in a volume of 100 µl or more, or 200 µl more, or 300 µl or more. Suitably, the spheroids are cultured in Corning® spheroid microplates.

3-dimensional cell culture matrices or scaffolds can be used for spheroid culture. These are often porous substrates that can support 3-dimensional cell growth and differentiation. A variety of materials have been developed to produce 3-dimensional scaffolds with differences in physical appearance, porosity, permeability, mechanical characteristics, and nano-scale surface morphology. Examples of such materials include: collagen gels, sponges or biogels; fibrin; fibronectin; laminin; alginates, hydrogels; cross-linked glycosaminoglyca; polymer-based scaffold, synthetic scaffolds; peptide scaffolds; and chitosan composite scaffolds.

3-dimensional spheroids more closely resemble in vivo tissue in terms of their cellular communication and development of extracellular matrices. These matrices assist the cells in moving within the spheroid similar to the way cells would move in living tissue. The spheroids are thus much improved models for differentiation, survival, cell migration, cell polarisation, gene expression and growth.

Spheroids can be harvested and studied using various methods well known in the art, including colorimetric, fluorescence, and luminescence assays measured with a plate reader or they can be readily observed by microscopy. Additional techniques include western, northern or southern blot, histological techniques (for example, immunohistrochemistry, in situ hybridization, immunoflourescence) and the like. The use of optical imaging methods—such as inverse bright field microscopy, fluorescence microscopy, single-photon emission computed tomography (SPECT), positron emission topography (PET), magnetic resonance imaging (MRI) and Cerenkov luminescence imaging (CLI) techniques is also contemplated.

Applications of the use of 3-dimensional spheroids include the study of the proliferation of cells and tissues in vitro in an environment that more closely approximates that found in vivo, the screening of compounds, toxicology assays, cell therapy, cell delivery, drug delivery, biochemical replacement, production of biologically active molecules, tissue engineering, biomaterial, and clinical trials.

The use of spheroids in 3-dimensional cell culture is generally reviewed in *Expert Opin. Drug Discov.* (2015) 10, 519-540.

In one embodiment, the spheroid is or is derived from a liver cell to form a 3-dimensional liver spheroid. Such liver spheroids can be prepared using various methods that are known in the art and described in, for example, *ALTEX* (2014) 31, 441-477 and *Toxicol. Sci. Off. J. Soc. Toxicol.* (2013) 133, 67-78.

One aspect relates to an isolated 3-dimensional liver spheroid wherein said spheroid has: increased ATP content as compared to a 3-dimensional liver spheroid cultured in Complete William's E medium alone; the same or increased activity of cytochrome P450 1A1 and cytochrome P450 1B1 as compared to a 3-dimensional liver spheroid cultured in Complete William's E medium alone; and increased albumin secretion as compared to a 3-dimensional liver spheroid cultured in Complete William's E medium alone.

Another aspect relates to an isolated 3-dimensional liver spheroid for use in a 3-dimensional multi-organ culture system obtained or obtainable by a process comprising: culturing a 3-dimensional liver spheroid in a cell culture medium comprising or consisting or consisting essentially of either: (a) Complete PneumaCult-ALI medium; or (b) Complete B-ALI medium; or (c) Complete PneumaCult-ALI medium and Complete William's E medium, or (d) Complete B-ALI medium and Complete William's E medium, for a period of time that is sufficient to obtain a 3-dimensional liver spheroid in which: ATP content is increased as compared to a 3-dimensional liver spheroid cultured in Complete William's E medium alone; cytochrome P450 1A1 and cytochrome P450 1B1 activity is the same or increased as compared to a 3-dimensional liver spheroid cultured in Complete William's E medium alone; and albumin secretion is increased as compared to a 3-dimensional liver spheroid cultured in Complete William's E medium alone.

Suitably, the isolated 3-dimensional liver spheroid can show improved characteristics as compared to isolated 3-dimensional liver spheroids grown in cell culture medium previously optimised for the culture of liver cells—such as William's E medium.

The isolated 3-dimensional liver spheroids can have increased ATP content, the same or increased activity of cytochrome P450 1A1 and cytochrome P450 1B1 and increased albumin secretion as compared to an isolated 3-dimensional liver spheroid cultured in Complete William's E medium alone.

The isolated 3-dimensional liver spheroid can have an ATP content that is at least 1.5 fold higher than an isolated 3-dimensional liver spheroid cultured in Complete William's E medium alone, cytochrome P450 1A1 and cytochrome P450 1B1 activity that is at least 1.0 fold higher as compared to an isolated 3-dimensional liver spheroid cultured in Complete William's E medium alone and increased albumin secretion that is at least 1.9 fold higher as compared to a 3-dimensional liver spheroid cultured in Complete William's E medium alone.

The isolated 3-dimensional liver spheroid can have an ATP content that is at least 2.1 fold higher than an isolated 3-dimensional liver spheroid cultured in Complete William's E medium alone, cytochrome P450 1A1 and cytochrome P450 1B1 activity that is at least 1.9 fold higher as compared to an isolated 3-dimensional liver spheroid cultured in Complete William's E medium alone and increased albumin secretion that is at least 1.8 fold higher as compared to a 3-dimensional liver spheroid cultured in Complete William's E medium alone.

The isolated 3-dimensional liver spheroid can have an ATP content that is at least 2.1 fold higher than an isolated 3-dimensional liver spheroid cultured in Complete William's E medium alone, cytochrome P450 1A1 and cytochrome P450 1B1 activity that is at least 2.1 fold higher as compared to an isolated 3-dimensional liver spheroid cultured in Complete William's E medium alone and increased albumin secretion that is at least 2.0 fold higher as compared to a 3-dimensional liver spheroid cultured in Complete William's E medium alone.

The isolated 3-dimensional liver spheroid can have an ATP content that is at least 2.4 fold higher than an isolated 3-dimensional liver spheroid cultured in Complete William's E medium alone, cytochrome P450 1A1 and cytochrome P450 1B1 activity that is at least 2.4 fold higher as compared to an isolated 3-dimensional liver spheroid cultured in Complete William's E medium alone and increased albumin secretion that is at least 2.1 fold higher as compared to a 3-dimensional liver spheroid cultured in Complete William's E medium alone.

The isolated 3-dimensional liver spheroid can have an ATP content that is at least 2.9 fold higher than an isolated 3-dimensional liver spheroid cultured in Complete William's E medium alone, cytochrome P450 1A1 and cytochrome P450 1B1 activity that is at least 2.3 fold higher as compared to an isolated 3-dimensional liver spheroid cultured in Complete William's E medium alone and increased albumin secretion that is at least 2.6 fold higher as compared to a 3-dimensional liver spheroid cultured in Complete William's E medium alone.

The isolated 3-dimensional liver spheroid can have an ATP content that is at least 2.6 fold higher than an isolated 3-dimensional liver spheroid cultured in Complete William's E medium alone, cytochrome P450 1A1 and cytochrome P450 1B1 activity that is at least 2.9 fold higher as compared to an isolated 3-dimensional liver spheroid cultured in complete William's E medium alone and increased albumin secretion that is at least 2.5 fold higher as compared to a 3-dimensional liver spheroid cultured in Complete William's E medium alone.

The isolated 3-dimensional liver spheroid can have an ATP content that is at least 2.7 fold higher than an isolated 3-dimensional liver spheroid cultured in Complete William's E medium alone, cytochrome P450 1A1 and cytochrome P450 1B1 activity that is at least 2.1 fold higher as compared to an isolated 3-dimensional liver spheroid cultured in complete William's E medium alone and increased albumin secretion that is at least 3.3 fold higher as compared to a 3-dimensional liver spheroid cultured in Complete William's E medium alone.

The isolated 3-dimensional liver spheroid can have an ATP content that is at least 2.7 fold higher than an isolated 3-dimensional liver spheroid cultured in Complete William's E medium alone, cytochrome P450 1A1 and cytochrome P450 1B1 activity that is at least 2.6 fold higher as compared to an isolated 3-dimensional liver spheroid cultured in complete William's E medium alone and increased albumin secretion that is at least 3.1 fold higher as compared to a 3-dimensional liver spheroid cultured in Complete William's E medium alone.

Methods of measuring ATP content, cytochrome P450 1A1 and cytochrome P450 1B1 activity and albumin secretion are described herein.

Suitably, the isolated 3-dimensional liver spheroid when grown in culture has the same number or an increased number of necrotic cells as compared to a 3-dimensional liver spheroid cultured in Complete William's E medium alone.

Suitably, the isolated 3-dimensional liver spheroid when grown in culture has an increased number of apoptotic cells as compared to a 3-dimensional liver spheroid cultured in Complete William's E medium alone.

Suitably, the isolated 3-dimensional liver spheroid has modulated (for example, increased or decreased) levels of glutathione (GSH) as compared to a 3-dimensional liver spheroid cultured in Complete William's E medium alone.

Suitably, the isolated 3-dimensional liver spheroid has increased levels of oxidized glutathione (GSSG) as compared to a 3-dimensional liver spheroid cultured in Complete William's E medium alone.

Suitably, the changes described herein are observed after 9 days of culture.

The use of co-cultures is also contemplated. In one aspect, there is provided a co-culture comprising the 3-dimensional liver spheroid as described herein together with at least one other cell type, suitably, a 3-dimensional lung epithelial cell. Suitably, the co-culture is maintained in a cell culture medium as described herein.

In one embodiment, the spheroid is or is derived from a lung cell to form a 3-dimensional lung spheroid. Such lung spheroids can be prepared using various methods that are known in the art, such as those described in *ALTEX* (2014) 31, 441-477 and *Toxicol. Sci. Off. J. Soc. Toxicol.* (2013) 133, 67-78.

Cell Sources

The present disclosure utilises various cell types including lung cells and liver cells. Cells and cell lines for use in the present disclosure can be isolated from a tissue or a fluid using methods that are well known in the art. Cells and cell lines for use in the present disclosure can be differentiated from stem cells—such as embryonic stem cells or induced pluripotent stem cells, or directly differentiated from somatic cells. Cells and cell lines may be or may be derived from human or animal subjects or from human or animal cells, including any of a number of mammalian species, suitably human, but including rat, mouse, pig, rabbit, and non-human primates and the like. Cells and cell lines can be obtained from commercial sources.

Lung cells—including lung epithelial cells—are one cell type of interest. Bronchial and/or airway epithelial cells are of particular use in the present disclosure. Human bronchial epithelial cells can be collected by brushing donor lungs during a bronchoscopy procedure. In one embodiment, the lung cells are Normal Human Bronchial Epithelial (NHBE) cells. The lung epithelial cells can be cultured as a monolayer of undifferentiated cells or further developed into an organotypic lung epithelium-like tissue at an air-liquid interface. Cells can be established at an air-liquid interface using the following methodology. Briefly, epithelial cells can be cultured in a flask to increase the number of cells. After a period of incubation, cells are detached from the flask, counted and seeded onto inserts. On these inserts, cells are incubated with medium on the apical and basal sides. This phase ensure that the cells will divide and completely cover the insert to form an epithelium. Then, apical medium is removed, the basal medium is retained and replaced with a more complete medium. Cultures are incubated like this for a further period of time. In the meantime, the cells will differentiate into 3 cell types: basal, goblet and ciliated cells. At the end of the maturation, the cultures are ready to use. The use of the air liquid interface to culture human nasal epithelial cells is described in *J Vis Exp.* 2013; (80): 50646.

Lung epithelial cells can be obtained from human or animal subjects with different pathologies, including subjects that are classified as smokers or non-smokers.

Liver cells are another cell type of interest. In one embodiment, the cells used are hepatocytes. Hepatocytes are cells of the liver, which make up 70-85% of the liver's cytoplasmic mass. The functionality of hepatocytes is highly dependent on their capacity to form a polar phenotype, which is only established in 3-dimensional culture. One source of liver cells is primary hepatocytes which are an in vitro model widely used to investigate numerous aspects of liver physiology and pathology. The technique used to isolate human hepatocytes can be based on a two-step collagenase perfusion of a donated liver. However, these cells do not express metabolic enzymes for more than 5 days. Another limitation is their short viability. These drawbacks can be overcome by the use of alternative, long-lived liver cell lines—such as human or animal hepatic progenitor cell lines. One such example of a human hepatic progenitor cell line is the HepaRG cell line (ThermoFisher Scientific). HepaRG cells retain many characteristics of primary human hepatocytes. They have greater liver-specific and metabolic gene expression compared to primary hepatocytes and a longer lifespan. Reorganisation of HepaRG cells in 3-dimensional spheroids further increases both the lifespan and metabolic capabilities, suggesting that spheroids may provide a better alternative in vitro liver model for toxicity testing. Liver spheroids can also be created with a mixture of primary hepatocytes and liver stellate cells or primary hepatocytes and adipose tissue-derived stem cells.

In one embodiment, the lung cell is a lung epithelial cell—such as a bronchial and/or airway epithelial cell.

In one embodiment, the liver cell is a HepaRG cell, suitably, a spheroid HepaRG cell. Combinations of cells are also contemplated, including combinations of liver and lung cells. The combination of a lung epithelial cell—such as a bronchial and/or airway epithelial cell, and a HepaRG cell, suitably, a spheroid HepaRG cell is contemplated. One aspect of the present disclosure relates to a 3-dimensional multi-organ culture system. This culture system can comprise the use of various cells—such as liver cells and a lung cells as described herein. The use of other cell types is also contemplated including, but not limited to, endothelial cells, (lung) fibroblasts and immune cells—such as monocytes/macrophages, dendritic cells, neutrophils and mast cells.

In one embodiment, the methods of the present disclosure exclude the step of isolating or obtaining a cell sample from a subject.

Cell Culture Media

One aspect of the present disclosure relates to cell culture media that can be used to culture 3-dimensional cells. In one embodiment, the cell culture media can be used to culture liver and lung cells without the loss of each of the cells individual characteristics. The liver cells that are cultured in the media described herein can even show improved characteristics as compared to liver cells grown in cell culture medium previously optimised for the culture of liver cells—such as Williams E medium. Suitably, the lung cells retain their characteristics as described herein. The media described herein can be used for the culture of liver cells or the culture of lung cells or the co-culture of liver cells and lung cells.

Suitably, liver cells grown in the cell culture medium/media can have increased ATP content, the same or increased activity of cytochrome P450 1A1 and cytochrome P450 1B1 and increased albumin secretion as compared to an isolated 3-dimensional liver spheroid cultured in Complete William's E medium alone.

Liver cells grown in the cell culture medium/media can have an ATP content that is at least 1.5 fold higher than an isolated 3-dimensional liver spheroid cultured in Complete William's E medium alone, cytochrome P450 1A1 and cytochrome P450 1B1 activity that is at least 1.0 fold higher and albumin secretion that is at least 1.9 fold higher as compared to a cell cultured in Complete William's E medium alone.

Liver cells grown in the cell culture medium/media can have an ATP content that is at least 2.1 fold higher, cytochrome P450 1A1 and cytochrome P450 1B1 activity that is at least 1.9 fold higher and increased albumin secretion that is at least 1.8 fold higher as compared to a cell cultured in Complete William's E medium alone.

Liver cells grown in the cell culture medium/media can have an ATP content that is at least 2.1 fold higher, cytochrome P450 1A1 and cytochrome P450 1B1 activity that is at least 2.1 fold higher and albumin secretion that is at least 2.0 fold higher as compared to a cell cultured in Complete William's E medium alone.

Liver cells grown in the cell culture medium/media can have an ATP content that is at least 2.4 fold higher, cytochrome P450 1A1 and cytochrome P450 1B1 activity that is at least 2.4 fold higher and albumin secretion that is at least 2.1 fold higher as compared to a cell cultured in Complete William's E medium alone.

Liver cells grown in the cell culture medium/media can have an ATP content that is at least 2.9 fold higher, cytochrome P450 1A1 and cytochrome P450 1B1 activity that is at least 2.3 fold higher and albumin secretion that is at least 2.6 fold higher as compared to a cell cultured in Complete William's E medium alone.

Liver cells grown in the cell culture medium/media can have an ATP content that is at least 2.6 fold higher, cytochrome P450 1A1 and cytochrome P450 1B1 activity that is at least 2.9 fold higher and albumin secretion that is at least 2.5 fold higher as compared to a cell cultured in Complete William's E medium alone.

Liver cells grown in the cell culture medium/media can have an ATP content that is at least 2.7 fold higher, cytochrome P450 1A1 and cytochrome P450 1B1 activity that is at least 2.1 fold higher and albumin secretion that is at least 3.3 fold higher as compared to a cell cultured in Complete William's E medium alone.

Liver cells grown in the cell culture medium/media can have an ATP content that is at least 2.7 fold higher, cytochrome P450 1A1 and cytochrome P450 1B1 activity that is at least 2.6 fold higher and albumin secretion that is at least 3.1 fold higher as compared to a cell cultured in Complete William's E medium alone.

Methods of measuring ATP content, cytochrome P450 1A1 and cytochrome P450 1B1 activity and albumin secretion are described herein.

Suitably, liver cells grown in the cell culture medium/media have the same number or an increased number of necrotic cells as compared to cells cultured in William's E medium alone.

Suitably, liver cells grown in the cell culture medium/media have an increased number of apoptotic cells as compared to cells cultured in William's E medium alone.

Suitably, liver cells grown in the cell culture medium/media have modulated (for example, increased or decreased) levels of glutathione (GSH) as compared to cells cultured in William's E medium alone.

Suitably, liver cells grown in the cell culture medium/media have increased levels of oxidized glutathione (GSSG) as compared to cells cultured in William's E medium alone.

Suitably, the changes described herein are observed after 9 days of culture.

Methods of measuring ATP content, cytochrome P450 1A1 and cytochrome P450 1B1 activity and albumin secretion are described in detail in the Examples. ATP content can be determined using the CellTiterGlo® assay (Promega, Dübendorf, Switzerland). Activity of CYP1A1/B1, CYP1A2, and CYP2B6 can be determined using the P450-Glo Assays (Promega, Dübendorf, Switzerland). Albumin secretion can be determined using the Human Albumin ELISA kit (Abcam).

Suitably, lung cells grown in the cell culture medium/media maintain viability, structural integrity and functional capabilities. Suitably, lung cells grown in the cell culture medium/media maintain the same viability, structural integrity and functional capabilities as compared to a lung cell cultured in Complete PneumaCult-ALI medium or Complete B-ALI medium. Suitably, lung cells grown in the cell culture medium/media are the same as lung cells cultured in Complete PneumaCult-ALI medium or Complete B-ALI medium.

The culture medium can be Complete PneumaCult-ALI medium which contains 100% (v/v) Complete PneumaCult-ALI medium without any addition or dilution thereto.

The culture medium can be Complete B-ALI medium which contains 100% (v/v) Complete B-ALI medium without any addition or dilution thereto.

The culture medium can be a mixture comprising or consisting or consisting essentially of Complete PneumaCult-ALI medium and Complete William's E medium. Complete PneumaCult-ALI medium is diluted with Complete William's E medium. In one embodiment, the mixture comprises or consists of from 30% to 99.9% (v/v), from 40% to 99.9% (v/v), from 50% to 99.9% (v/v), from 60% to 99.9% (v/v), from 70% to 99.9% (v/v) Complete PneumaCult-ALI medium with the remaining volume being made up to 100% (v/v) with Complete William's E medium.

The culture medium can be a mixture comprising or consisting or consisting essentially of a mixture comprising or consisting or consisting essentially of Complete B-ALI medium and Complete William's E medium. Complete B-ALI medium is diluted with Complete William's E medium. In one embodiment, the mixture comprises or consists of 30% to 99.9% (v/v), from 40% to 99.9% (v/v), from 50% to 99.9% (v/v), from 60% to 99.9% (v/v), from 70% to 99.9% (v/v) Complete B-ALI medium with the remaining volume being made up to 100% (v/v) with Complete William's E medium.

(i) Complete B-ALI Medium

In one embodiment, the cell culture medium consists of complete B-ALI medium. In other words, the cell culture medium contains 100% (v/v) complete B-ALI medium with no added culture medium constituents. In another embodiment, the cell culture medium consists essentially of complete B-ALI medium Complete B-ALI Medium Promotes the Differentiation of Lung Epithelium Cells.

Complete B-ALI medium is prepared by combining together the contents of the B-ALI BulletKit (Lonza, catalogue number 193514), containing the B-ALI growth basal medium, B-ALI differentiation basal medium, and BALI SingleQuots kit. The B-ALI BulletKit is made up of a Growth and Differentiation Medium SingleQuots Kit, Growth Basal Medium and Differentiation Basal Medium. It promotes full differentiation of lung epithelial cells.

According to this embodiment of the disclosure, a 3-dimensional liver spheroid cultured in complete B-ALI medium alone (ie. 100% (v/v) complete B-ALI medium) for 9 days has: (A) increased ATP content as compared to a 3-dimensional liver spheroid cultured in Complete William's E medium alone (ie. 100% (v/v) Complete William's E medium) for the same period of time; (B) the same or increased activity of cytochrome P450 1A1 and cytochrome P450 1B1 as compared to a 3-dimensional liver spheroid cultured in Complete William's E medium alone (ie. 100% (v/v) Complete William's E medium) for the same period of time; and (C) increased albumin secretion as compared to a 3-dimensional liver spheroid cultured in Complete William's E medium alone (ie. 100% (v/v) Complete William's E medium) for the same period of time. Suitably, the changes described herein are observed after 9 days of culture.

Suitably, a 3-dimensional liver spheroid cultured in complete B-ALI medium alone (ie. 100% (v/v) complete B-ALI medium) for 9 days has: (A) a 1.9-fold increased ATP content as compared to a 3-dimensional liver spheroid cultured in Complete William's E medium alone (ie. 100% (v/v) Complete William's E medium) for the same period of time; (B) the same activity of cytochrome P450 1A1 and cytochrome P450 1B1 as compared to a 3-dimensional liver spheroid cultured in Complete William's E medium alone (ie. 100% (v/v) Complete William's E medium) for the same period of time; and (C) a 1.9-fold increased albumin secretion as compared to a 3-dimensional liver spheroid cultured in Complete William's E medium alone (ie. 100% (v/v) Complete William's E medium) for the same period of time (see Table 1). Suitably, the changes described herein are observed after 9 days of culture.

In another embodiment, the cell culture medium comprises complete B-ALI medium with the proviso that a 3-dimensional liver spheroid cultured in the cell culture medium comprising Complete B-ALI medium after 9 days has: (A) increased ATP content as compared to a 3-dimensional liver spheroid cultured in Complete William's E medium alone; (B) the same activity of cytochrome P450 1A1 and cytochrome P450 1B1 as compared to a 3-dimensional liver spheroid cultured in Complete William's E medium alone; and (C) increased albumin secretion as compared to a 3-dimensional liver spheroid cultured in William's E medium alone. Suitably, the changes described herein are observed after 9 days of culture.

Suitably, the cell culture medium comprises complete B-ALI medium with the proviso that a 3-dimensional liver spheroid cultured in the cell culture medium comprising complete B-ALI medium after 9 days has: (A) a 1.9-fold increased ATP content as compared to a 3-dimensional liver spheroid cultured in Complete William's E medium alone (ie. 100% (v/v) Complete William's E medium) for the same period of time; (B) the same activity of cytochrome P450 1A1 and cytochrome P450 1B1 as compared to a 3-dimensional liver spheroid cultured in Complete William's E medium alone (ie. 100% (v/v) Complete William's E medium) for the same period of time; and (C) a 1.9-fold increased albumin secretion as compared to a 3-dimensional liver spheroid cultured in Complete William's E medium alone (ie. 100% (v/v) Complete William's E medium) for the same period of time (see Table 1).

Suitably, the isolated 3-dimensional liver spheroid when grown in culture has an increased number of apoptotic cells as compared to a 3-dimensional liver spheroid cultured in William's E medium alone.

Suitably, the isolated 3-dimensional liver spheroid has modulated (for example, increased or decreased) levels of glutathione (GSH) as compared to a 3-dimensional liver spheroid cultured in William's E medium alone.

Suitably, the isolated 3-dimensional liver spheroid has increased levels of oxidized glutathione (GSSG) as compared to a 3-dimensional liver spheroid cultured in William's E medium alone.

Suitably, the changes described herein are observed after 9 days of culture.

(ii) Complete B-ALI Medium and Complete William's E Medium.

In one embodiment, the cell culture medium comprises or consists or consists essentially of a mixture of Complete B-ALI medium and Complete William's E medium. Complete William's E medium is developed for the isolation and long term maintenance of adult rat liver epithelial cells.

Complete B-ALI medium is prepared by combining together the contents of the B-ALI BulletKit (Lonza, catalogue number 193514), containing the B-ALI growth basal medium, B-ALI differentiation basal medium, and BALI SingleQuots kit. The B-ALI BulletKit is made up of a Growth and Differentiation Medium SingleQuots Kit, Growth Basal Medium and Differentiation Basal Medium. It promotes full differentiation of airway epithelium.

Complete William's E medium is prepared by supplementing William's E medium (ThermoFisher Scientific, catalogue number 12551032) with HepaRG Maintenance & Metabolism Supplement (ThermoFisher Scientific, catalogue number HPRG720) and GlutaMAX™ solution (ThermoFisher Scientific, catalogue number 35050061). William's E medium is described in *Exp. Cell Res.* (1974) 89:139 and shown in Table 2. Complete B-ALI medium is mixed with Complete William's E medium. The percentages of each medium that are combined together can be varied. In one embodiment, the mixture comprises, consists or consists essentially of at least 70% (v/v) Complete B-ALI medium with the remaining volume being made up to 100% (v/v) with Complete William's E medium. In one embodiment, the mixture comprises, consists or consists essentially of 70%/30% (v/v) Complete B-ALI medium/Complete William's E medium. In another embodiment, the mixture comprises, consists or consists essentially of 75%/25% (v/v) Complete B-ALI medium/Complete William's E medium. In another embodiment, the mixture comprises, consists or consists essentially of 80%/20% (v/v) Complete B-ALI medium/Complete William's E medium. In another embodiment, the mixture comprises, consists or consists essentially of 85%/15% (v/v) Complete B-ALI medium/Complete William's E medium. In another embodiment, the mixture comprises, consists or consists essentially of 90%/10% (v/v) Complete B-ALI medium/Complete William's E medium. In another embodiment, the mixture comprises, consists or consists essentially of 95%/5% (v/v) Complete B-ALI medium/Complete William's E medium.

Suitably, when the mixture comprises, consists or consists essentially of 90%/10% (v/v) Complete B-ALI medium/Complete William's E medium a 3-dimensional liver spheroid cultured in the cell culture medium after 9 days has: (A) increased ATP content as compared to a 3-dimensional liver spheroid cultured in Complete William's E medium alone; (B) increased activity of cytochrome P450 1A1 and cytochrome P450 1B1 as compared to a 3-dimensional liver spheroid cultured in Complete William's E medium alone; and (C) increased albumin secretion as compared to a 3-dimensional liver spheroid cultured in William's E medium alone. Suitably, the changes described herein are observed after 9 days of culture.

Suitably, when the mixture comprises, consists or consists essentially of 90%/10% (v/v) Complete B-ALI medium/Complete William's E medium a 3-dimensional liver spheroid cultured in the cell culture medium after 9 days has: (A) a 2.1-fold increased ATP content as compared to a 3-dimensional liver spheroid cultured in Complete William's E medium alone (ie. 100% (v/v) Complete William's E medium) for the same period of time; (B) a 1.9-fold increased activity of cytochrome P450 1A1 and cytochrome P450 1B1 as compared to a 3-dimensional liver spheroid cultured in Complete William's E medium alone (ie. 100% (v/v) Complete William's E medium) for the same period of time; and (C) a 1.8-fold increased albumin secretion as compared to a 3-dimensional liver spheroid cultured in Complete William's E medium alone (ie. 100% (v/v) Complete William's E medium) for the same period of time (see Table 1). Suitably, the changes described herein are observed after 9 days of culture.

Suitably, when the mixture comprises, consists or consists essentially of 80%/20% (v/v) Complete B-ALI medium/Complete William's E medium a 3-dimensional liver spheroid cultured in the cell culture medium after 9 days has: (A) increased ATP content as compared to a 3-dimensional liver spheroid cultured in Complete William's E medium alone; (B) increased activity of cytochrome P450 1A1 and cytochrome P450 1B1 as compared to a 3-dimensional liver spheroid cultured in Complete William's E medium alone; and (C) increased albumin secretion as compared to a 3-dimensional liver spheroid cultured in William's E medium alone. Suitably, the changes described herein are observed after 9 days of culture.

Suitably, when the mixture comprises, consists or consists essentially of 80%/20% (v/v) Complete B-ALI medium/Complete William's E medium a 3-dimensional liver spheroid cultured in the cell culture medium after 9 days has: (A) a 2.4-fold increased ATP content as compared to a 3-dimensional liver spheroid cultured in Complete William's E medium alone (ie. 100% (v/v) Complete William's E medium) for the same period of time; (B) a 2.4-fold increased activity of cytochrome P450 1A1 and cytochrome P450 1B1 as compared to a 3-dimensional liver spheroid cultured in Complete William's E medium alone (ie. 100% (v/v) Complete William's E medium) for the same period of time; and (C) a 2.1-fold increased albumin secretion as compared to a 3-dimensional liver spheroid cultured in Complete William's E medium alone (ie. 100% (v/v) Complete William's E medium) for the same period of time (see Table 1). Suitably, the changes described herein are observed after 9 days of culture.

Suitably, when the mixture comprises, consists or consists essentially of 70%/30% (v/v) Complete B-ALI medium/Complete William's E medium a 3-dimensional liver spheroid cultured in the cell culture medium after 9 days has: (A) increased ATP content as compared to a 3-dimensional liver spheroid cultured in Complete William's E medium alone; (B) increased activity of cytochrome P450 1A1 and cytochrome P450 1B1 as compared to a 3-dimensional liver spheroid cultured in Complete William's E medium alone; and (C) increased albumin secretion as compared to a 3-dimensional liver spheroid cultured in William's E medium alone. Suitably, the changes described herein are observed after 9 days of culture.

Suitably, when the mixture comprises, consists or consists essentially of 70%/30% (v/v) Complete B-ALI medium/Complete William's E medium a 3-dimensional liver spheroid cultured in the cell culture medium after 9 days has: (A) a 2.1-fold increased ATP content as compared to a 3-dimensional liver spheroid cultured in Complete William's E medium alone (ie. 100% (v/v) Complete William's E medium) for the same period of time; (B) a 2.1-fold increased activity of cytochrome P450 1A1 and cytochrome P450 1B1 as compared to a 3-dimensional liver spheroid cultured in Complete William's E medium alone (ie. 100% (v/v) Complete William's E medium) for the same period of time; and (C) a 2.0-fold increased albumin secretion as compared to a 3-dimensional liver spheroid cultured in Complete William's E medium alone (ie. 100% (v/v) Complete William's E medium) for the same period of time (see Table 1). Suitably, the changes described herein are observed after 9 days of culture.

As can be seen from the results summarised in Table 1, the mixture of 80%/20% (v/v) complete B-ALI medium/complete William's E medium resulted in a combined 6.9-fold increase in ATP content, cytochrome P450 1A1 and cytochrome P450 1B1 activity and albumin secretion as compared to a 3-dimensional liver spheroid cultured in Complete William's E medium alone. It is therefore fully excepted that further dilutions of the complete B-ALI medium in Complete William's E medium will result in a combined increase in ATP content, cytochrome P450 1A1 and cytochrome P450 1B1 activity as compared to a 3-dimensional liver spheroid cultured in Complete William's E medium alone. 60%/40% (v/v) complete B-ALI medium/Complete William's E medium, 50%/50% (v/v) complete B-ALI medium/Complete William's E medium, 40%/60% (v/v) complete B-ALI medium/Complete William's E medium, and 30%/70% (v/v) complete B-ALI medium/Complete William's E medium is disclosed.

Suitably, the isolated 3-dimensional liver spheroid when grown in culture has an increased number of apoptotic cells as compared to a 3-dimensional liver spheroid cultured in William's E medium alone.

Suitably, the isolated 3-dimensional liver spheroid has modulated (for example, increased or decreased) levels of glutathione (GSH) as compared to a 3-dimensional liver spheroid cultured in William's E medium alone.

Suitably, the isolated 3-dimensional liver spheroid has increased levels of oxidized glutathione (GSSG) as compared to a 3-dimensional liver spheroid cultured in William's E medium alone.

Suitably, the changes described herein are observed after 9 days of culture.

(iii) Complete PneumaCult-ALI Medium.

In one embodiment, the cell culture medium consists of complete PneumaCult-ALI medium. In other words, the cell culture medium contains 100% (v/v) complete PneumaCult-ALI medium with no added culture medium constituents. In another embodiment, the cell culture medium consists essentially of complete PneumaCult-ALI medium.

PneumaCult-ALI medium promotes the differentiation of lung epithelial cells.

Complete PneumaCult-ALI medium is prepared by mixing PneumaCult-ALI Basal Medium (StemCell Technologies, ref. 05002) with PneumaCult-ALI 10× Supplement (StemCell Technologies, ref. 05003), PneumaCult-ALI Maintenance Supplement (StemCell Technologies, ref. 05006), Hydrocortisone Stock Solution (StemCell Technologies, ref. 07925) and 0.2% Heparin Sodium Salt in PBS (StemCell Technologies, ref. 37250).

According to this embodiment of the disclosure, a 3-dimensional liver spheroid cultured in complete PneumaCult-ALI medium alone (ie. 100% (v/v) complete PneumaCult-ALI medium) for 9 days has: (A) increased ATP content as compared to a 3-dimensional liver spheroid cultured in Complete William's E medium alone (ie. 100% (v/v) Complete William's E medium) for the same period of time; (B) increased activity of cytochrome P450 1A1 and cytochrome P450 1B1 as compared to a 3-dimensional liver spheroid cultured in Complete William's E medium alone (ie. 100% (v/v) Complete William's E medium) for the same period of time; and (C) increased albumin secretion as compared to a 3-dimensional liver spheroid cultured in Complete William's E medium alone (ie. 100% (v/v) Complete William's E medium) for the same period of time. Suitably, the changes described herein are observed after 9 days of culture.

Suitably, a 3-dimensional liver spheroid cultured in complete PneumaCult-ALI medium alone (ie. 100% (v/v) complete PneumaCult-ALI medium) for 9 days has: (A) a 2.7-fold increased ATP content as compared to a 3-dimensional liver spheroid cultured in Complete William's E medium alone (ie. 100% (v/v) Complete William's E medium) for the same period of time; (B) a 2.1-fold increased activity of cytochrome P450 1A1 and cytochrome P450 1B1 as compared to a 3-dimensional liver spheroid cultured in Complete William's E medium alone (ie. 100% (v/v) Complete William's E medium) for the same period of time; and (C) a 3.3-fold increased albumin secretion as compared to a 3-dimensional liver spheroid cultured in Complete William's E medium alone (ie. 100% (v/v) Complete William's E medium) for the same period of time (see Table 1). Suitably, the changes described herein are observed after 9 days of culture.

In another embodiment, the cell culture medium comprises complete PneumaCult-ALI medium with the proviso that a 3-dimensional liver spheroid cultured in the cell culture medium comprising complete PneumaCult-ALI medium after 9 days has: (A) increased ATP content as compared to a 3-dimensional liver spheroid cultured in Complete William's E medium alone; (B) increased activity of cytochrome P450 1A1 and cytochrome P450 1B1 as compared to a 3-dimensional liver spheroid cultured in Complete William's E medium alone; and (C) increased albumin secretion as compared to a 3-dimensional liver spheroid cultured in William's E medium alone. Suitably, the changes described herein are observed after 9 days of culture.

Suitably, the cell culture medium comprises complete PneumaCult-ALI medium with the proviso that a 3-dimensional liver spheroid cultured in the cell culture medium comprising complete PneumaCult-ALI medium after 9 days has: (A) a 2.7-fold increased ATP content as compared to a 3-dimensional liver spheroid cultured in Complete William's E medium alone (ie. 100% (v/v) Complete William's E medium) for the same period of time; (B) a 2.1-fold increased activity of cytochrome P450 1A1 and cytochrome P450 1B1 as compared to a 3-dimensional liver spheroid cultured in Complete William's E medium alone (ie. 100% (v/v) Complete William's E medium) for the same period of time; and (C) a 3.3-fold increased albumin secretion as compared to a 3-dimensional liver spheroid cultured in Complete William's E medium alone (ie. 100% (v/v) Complete William's E medium) for the same period of time (see Table 1). Suitably, the changes described herein are observed after 9 days of culture.

Suitably, the isolated 3-dimensional liver spheroid when grown in culture has an increased number of apoptotic cells as compared to a 3-dimensional liver spheroid cultured in William's E medium alone.

Suitably, the isolated 3-dimensional liver spheroid has modulated (for example, increased or decreased) levels of glutathione (GSH) as compared to a 3-dimensional liver spheroid cultured in William's E medium alone.

Suitably, the isolated 3-dimensional liver spheroid has increased levels of oxidized glutathione (GSSG) as compared to a 3-dimensional liver spheroid cultured in William's E medium alone.

Suitably, the changes described herein are observed after 9 days of culture.

(iv) Complete PneumaCult-ALI Medium and Complete William's E Medium

In one embodiment, the cell culture medium comprises or consists of a mixture of Complete PneumaCult-ALI medium and Complete William's E medium.

Complete PneumaCult-ALI medium is prepared by mixing PneumaCult-ALI Basal Medium (StemCell Technologies, catalogue number 05002) with PneumaCult-ALI 10× Supplement (StemCell Technologies, catalogue number 05003), PneumaCult-ALI Maintenance Supplement (StemCell Technologies, catalogue number 05006), Hydrocortisone Stock Solution (StemCell Technologies, catalogue number 07925) and 0.2% Heparin Sodium Salt in PBS (StemCell Technologies, catalogue number 37250).

Complete William's E medium is prepared by supplementing William's E medium (ThermoFisher Scientific, catalogue number 12551032) with HepaRG Maintenance & Metabolism Supplement (ThermoFisher Scientific, catalogue number HPRG720) and GlutaMAX solution (ThermoFisher Scientific, catalogue number 35050061).

Complete PneumaCult-ALI medium is mixed with Complete William's E medium. The percentages of each medium that are combined together can be varied. In one embodiment, the mixture comprises, consists or consists essentially of at least 70% (v/v) Complete PneumaCult-ALI medium with the remaining volume being made up to 100% (v/v) with Complete William's E medium.

In one embodiment, the mixture comprises, consists or consists essentially of 70%/30% (v/v) Complete PneumaCult-ALI medium/Complete William's E medium. In another embodiment, the mixture comprises, consists or consists essentially of 75%/25% (v/v) Complete PneumaCult-ALI medium/Complete William's E medium. In another embodiment, the mixture comprises, consists or consists essentially of 80%/20% (v/v) Complete PneumaCult-ALI medium/

Complete William's E medium. In another embodiment, the mixture comprises, consists or consists essentially of 85%/15% (v/v) Complete PneumaCult-ALI medium/Complete William's E medium. In another embodiment, the mixture comprises, consists or consists essentially of 90%/10% (v/v) Complete PneumaCult-ALI medium/Complete William's E medium. In another embodiment, the mixture comprises, consists or consists essentially of 95%/5% (v/v) Complete PneumaCult-ALI medium/Complete William's E medium.

Suitably, when the mixture comprises, consists or consists essentially of 90%/10% (v/v) Complete PneumaCult-ALI medium/Complete William's E medium a 3-dimensional liver spheroid cultured in the cell culture medium after 9 days has: (A) increased ATP content as compared to a 3-dimensional liver spheroid cultured in Complete William's E medium alone; (B) increased activity of cytochrome P450 1A1 and cytochrome P450 1B1 as compared to a 3-dimensional liver spheroid cultured in Complete William's E medium alone; and (C) increased albumin secretion as compared to a 3-dimensional liver spheroid cultured in William's E medium alone. Suitably, the changes described herein are observed after 9 days of culture.

Suitably, when the mixture comprises, consists or consists essentially of 90%/10% (v/v) Complete PneumaCult-ALI/Complete William's E medium a 3-dimensional liver spheroid cultured in the cell culture medium after 9 days has: (A) a 2.9-fold increased ATP content as compared to a 3-dimensional liver spheroid cultured in Complete William's E medium alone (ie. 100% (v/v) Complete William's E medium) for the same period of time; (B) a 2.3-fold increased activity of cytochrome P450 1A1 and cytochrome P450 1B1 as compared to a 3-dimensional liver spheroid cultured in Complete William's E medium alone (ie. 100% (v/v) Complete William's E medium) for the same period of time; and (C) a 2.6-fold increased albumin secretion as compared to a 3-dimensional liver spheroid cultured in Complete William's E medium alone (ie. 100% (v/v) Complete William's E medium) for the same period of time (see Table 1). Suitably, the changes described herein are observed after 9 days of culture.

Suitably, when the mixture comprises, consists or consists essentially of 80%/20% (v/v) Complete PneumaCult-ALI medium/Complete William's E medium a 3-dimensional liver spheroid cultured in the cell culture medium after 9 days has: (A) increased ATP content as compared to a 3-dimensional liver spheroid cultured in Complete William's E medium alone; (B) increased activity of cytochrome P450 1A1 and cytochrome P450 1B1 as compared to a 3-dimensional liver spheroid cultured in Complete William's E medium alone; and (C) increased albumin secretion as compared to a 3-dimensional liver spheroid cultured in William's E medium alone. Suitably, the changes described herein are observed after 9 days of culture.

Suitably, when the mixture comprises, consists or consists essentially of 80%/20% (v/v) Complete PneumaCult-ALI/Complete William's E medium a 3-dimensional liver spheroid cultured in the cell culture medium after 9 days has: (A) a 2.7-fold increased ATP content as compared to a 3-dimensional liver spheroid cultured in Complete William's E medium alone (ie. 100% (v/v) Complete William's E medium) for the same period of time; (B) a 2.5-fold increased activity of cytochrome P450 1A1 and cytochrome P450 1B1 as compared to a 3-dimensional liver spheroid cultured in Complete William's E medium alone (ie. 100% (v/v) Complete William's E medium) for the same period of time; and (C) a 3.1-fold increased albumin secretion as compared to a 3-dimensional liver spheroid cultured in Complete William's E medium alone (ie. 100% (v/v) Complete William's E medium) for the same period of time (see Table 1). Suitably, the changes described herein are observed after 9 days of culture.

Suitably, when the mixture comprises, consists or consists essentially of 70%/30% (v/v) Complete PneumaCult-ALI medium/Complete William's E medium a 3-dimensional liver spheroid cultured in the cell culture medium after 9 days has: (A) increased ATP content as compared to a 3-dimensional liver spheroid cultured in Complete William's E medium alone; (B) increased activity of cytochrome P450 1A1 and cytochrome P450 1B1 as compared to a 3-dimensional liver spheroid cultured in Complete William's E medium alone; and (C) increased albumin secretion as compared to a 3-dimensional liver spheroid cultured in William's E medium alone. Suitably, the changes described herein are observed after 9 days of culture.

Suitably, when the mixture comprises, consists or consists essentially of 70%/30% (v/v) Complete PneumaCult-ALI/Complete William's E medium a 3-dimensional liver spheroid cultured in the cell culture medium after 9 days has: (A) a 2.6-fold increased ATP content as compared to a 3-dimensional liver spheroid cultured in Complete William's E medium alone (ie. 100% (v/v) Complete William's E medium) for the same period of time; (B) a 2.9-fold increased activity of cytochrome P450 1A1 and cytochrome P450 1B1 as compared to a 3-dimensional liver spheroid cultured in Complete William's E medium alone (ie. 100% (v/v) Complete William's E medium) for the same period of time; and (C) a 2.5-fold increased albumin secretion as compared to a 3-dimensional liver spheroid cultured in complete William's E medium alone (ie. 100% (v/v) Complete William's E medium) for the same period of time (see Table 1). Suitably, the changes described herein are observed after 9 days of culture.

Suitably, the isolated 3-dimensional liver spheroid when grown in culture has an increased number of apoptotic cells as compared to a 3-dimensional liver spheroid cultured in William's E medium alone.

Suitably, the isolated 3-dimensional liver spheroid has modulated (for example, increased or decreased) levels of glutathione (GSH) as compared to a 3-dimensional liver spheroid cultured in William's E medium alone.

Suitably, the isolated 3-dimensional liver spheroid has increased levels of oxidized glutathione (GSSG) as compared to a 3-dimensional liver spheroid cultured in William's E medium alone.

Suitably, the changes described herein are observed after 9 days of culture.

As can be seen from the results summarised in Table 1, the mixture of 70%/30% (v/v) complete PneumaCult-ALI/Complete William's E medium resulted in a combined 8-fold increase in ATP content, cytochrome P450 1A1 and cytochrome P450 1B1 activity and albumin secretion as compared to a 3-dimensional liver spheroid cultured in Complete William's E medium alone. It is therefore fully excepted that further dilution of the complete PneumaCult-ALI in Complete William's E medium will result in a combined increase in ATP content, cytochrome P450 1A1 and cytochrome P450 1B1 activity as compared to a 3-dimensional liver spheroid cultured in Complete William's E medium alone. 60%/40% (v/v) complete PneumaCult-ALI/Complete William's E medium, 50%/50% (v/v) complete PneumaCult-ALI/Complete William's E medium, 40%/60% (v/v) complete PneumaCult-ALI/Complete William's E medium, and 30%/70% (v/v) complete PneumaCult-ALI/Complete William's E medium is disclosed.

Of the various media tested in the present disclosure for the culture of 3-dimensional liver spheroids, the mixture consisting of 80%/20% (v/v) complete PneumaCult-ALI/Complete William's E medium resulted in the largest overall fold increase in ATP content, activity of cytochrome P450 1A1 and cytochrome P450 1B1 and albumin secretion of the 3-dimensional liver spheroids. A cell culture medium mixture comprising or consisting or consisting essentially of 80%/20% (v/v) complete PneumaCult-ALI/Complete William's E medium is preferred for certain embodiments of the present disclosure.

Of the various media tested in the present disclosure for the culture of 3-dimensional liver spheroids, the mixture consisting or consisting essentially of 100% (v/v) complete PneumaCult-ALI medium resulted in the second largest overall fold increase in ATP content, activity of cytochrome P450 1A1 and cytochrome P450 1B1 and albumin secretion of the 3-dimensional liver spheroids. A cell culture medium consisting or consisting essentially of 100% (v/v) complete PneumaCult-ALI medium is preferred for certain embodiments of the present disclosure.

Of the various media tested in the present disclosure for the culture of 3-dimensional liver spheroids, the mixture comprising, consisting or consisting essentially of 70%/30% (v/v) complete PneumaCult-ALI/Complete William's E medium resulted in the third largest overall fold increase in ATP content, activity of cytochrome P450 1A1 and cytochrome P450 1B1 and albumin secretion of the 3-dimensional liver spheroids. A cell culture medium mixture comprising or consisting or consisting essentially of 70%/30% (v/v) complete PneumaCult-ALI/Complete William's E medium is preferred for certain embodiments of the present disclosure.

Of the various media tested in the present disclosure for the culture of 3-dimensional liver spheroids, the mixture comprising, consisting or consisting essentially of 90%/10% (v/v) complete PneumaCult-ALI/Complete William's E medium resulted in the fourth largest overall fold increase in ATP content, activity of cytochrome P450 1A1 and cytochrome P450 1B1 and albumin secretion of the 3-dimensional liver spheroids. A cell culture medium mixture comprising or consisting or consisting essentially of 90%/10% (v/v) complete PneumaCult-ALI/Complete William's E medium is preferred for certain embodiments of the present disclosure.

Of the various media tested in the present disclosure for the culture of 3-dimensional liver spheroids, the mixture comprising, consisting or consisting essentially of 80%/20% (v/v) complete B-ALI medium/Complete William's E medium resulted in the fifth largest overall fold increase in ATP content, activity of cytochrome P450 1A1 and cytochrome P450 1B1 and albumin secretion of the 3-dimensional liver spheroids. A cell culture medium mixture comprising or consisting or consisting essentially of 80%/20% (v/v) complete B-ALI medium/Complete William's E medium is preferred for certain embodiments of the present disclosure.

Of the various media tested in the present disclosure for the culture of 3-dimensional liver spheroids, the mixture comprising, consisting or consisting essentially of 70%/30% (v/v) complete B-ALI medium/Complete William's E medium resulted in the sixth largest overall fold increase in ATP content, activity of cytochrome P450 1A1 and cytochrome P450 1B1 and albumin secretion of the 3-dimensional liver spheroids. A cell culture medium mixture comprising or consisting or consisting essentially of 70%/30% (v/v) complete B-ALI medium/Complete William's E medium is preferred for certain embodiments of the present disclosure.

Of the various media tested in the present disclosure for the culture of 3-dimensional liver spheroids, the mixture comprising, consisting or consisting essentially of 90%/10% (v/v) complete B-ALI medium/Complete William's E medium resulted in the seventh largest overall fold increase in ATP content, activity of cytochrome P450 1A1 and cytochrome P450 1B1 and albumin secretion of the 3-dimensional liver spheroids. A cell culture medium mixture comprising or consisting or consisting essentially of 90%/10% (v/v) complete B-ALI medium/Complete William's E medium is preferred for certain embodiments of the present disclosure.

Of the various media tested in the present disclosure for the culture of 3-dimensional liver spheroids, the mixture comprising, consisting or consisting essentially of 100% (v/v) complete B-ALI medium resulted in the eighth largest overall fold increase in ATP content, activity of cytochrome P450 1A1 and cytochrome P450 1B1 and albumin secretion of the 3-dimensional liver spheroids. A cell culture medium mixture comprising or consisting or consisting essentially of 100% (v/v) complete B-ALI medium is preferred for certain embodiments of the present disclosure.

A further aspect, relates to method for identifying a co-culture medium that can be used for the co-culture of the lung cells and liver cells described herein, comprising: (a) providing a culture medium comprising Complete PneumaCult-ALI medium or Complete William's E medium; (b) mixing the Complete PneumaCult-ALI medium or Complete William's E medium with a culture medium this is optimised for or specific for the culture of liver cells to provide a cell culture medium mixture; (c) adding a co-culture of lung cells and liver cells to the cell culture medium mixture: and (d) identifying a cell culture medium mixture in which the liver cell has: increased ATP content as compared to a liver cell cultured in Complete William's E medium alone; the same or increased activity of cytochrome P450 1A1 and cytochrome P450 1B1 as compared to a liver cell cultured in Complete William's E medium alone; and increased albumin secretion as compared to a liver cell cultured in William's E medium alone and the lung cell retains its characteristics. Other properties of the liver cell are described herein.

A further aspect, relates to a co-culture medium that can be used for the co-culture of lung cells and liver cells obtained or obtainable by this process, wherein a liver cell cultured in the co-culture medium has: increased ATP content as compared to a liver cell cultured in Complete William's E medium alone; the same or increased activity of cytochrome P450 1A1 and cytochrome P450 1B1 as compared to a liver cell cultured in Complete William's E medium alone; and increased albumin secretion as compared to a liver cell cultured in William's E medium alone and the lung cell retains its characteristics. Other properties of the liver cell are described herein.

3-Dimensional Organ Culture Systems 3-dimensional organ culture systems, especially those in miniaturised form, are of use in the present disclosure as they allow the study of how organs function. Response to certain stimuli, response to one or more chemical compounds or compositions and pharmacokinetic behaviour of such compounds or compositions can be studied, for example, in screening assays as described herein. Miniaturised 3-dimensional organ culture systems, also known as organ on-a-chip, are of particular interest as they allow the combined study of groups of organs, that is, the study of at least 3-dimensional lung and liver tissues. This allows the complexity of interaction between lung and liver tissues to be reproduced. The 3-dimensional culture system of the present disclosure which takes into account lung and liver organs and allows dynamic culture of these multiple organs is therefore highly advantageous. The majority of 3-dimensional organ culture systems are organotypic, which means that they seek to reproduce major functions of an organ or organ system. A miniaturised fluidic system interconnecting the lung and liver tissues is also described.

Suitably, the organ-on-a-chip is a microfluidic device that has at least one physiological function of at least one tissue type—such as lung or liver, or more suitably has at least one physiological function of at least two different tissue types—such as lung and liver. The organ-on-a-chip can be of any living tissue or organ from any organism including mammals, non-mammals, and animals.

The organ-on-a-chip will generally comprise at least one microfluidic channel disposed therein. The exact dimension of these channels will differ based on the function and/or dimensions of the chip. The at least one microfluidic channel will generally function to provide and replenish nutrients to the biological material on the chip.

In one aspect, the 3-dimensional multi-organ culture system comprises: (a) a first organ growth section adapted to culture or submerge a first 3-dimensional cell type—such as liver—in a culture medium; (b) a second organ growth section adapted to culture a second 3-dimensional cell type—such as lung—at an air liquid interface, the second 3-dimensional cell type being a cell type that is different than the first 3-dimensional cell type; and (c) a culture medium reservoir connecting the first organ cavity and the second organ cavity to allow for the flow of culture medium there between.

The first organ growth section can comprise a first organ cavity or receptacle or vessel or container or containment means.

The second organ growth section can comprise a second organ cavity or receptacle or vessel or container or containment means.

The reservoir can be provided by a microfluidic channel. Suitably, the first organ growth section—such as the first organ cavity—and the second organ growth section—such as the second organ cavity—contain the same culture medium—such as culture medium comprising or consisting or consisting essentially of: (a) Complete PneumaCult-ALI medium; or (b) Complete B-ALI medium; or (c) Complete PneumaCult-ALI medium and Complete William's E medium, or (d) Complete B-ALI medium and Complete William's E medium or a variation thereof as described herein.

In addition to the cell types described herein, the chip can comprise additional cell types to create a multi-organ chip.

The person skilled in the art is able to design a chip with the optimum number and/or dimension of channels required to achieve a particular application.

The chip can comprise a fluid control element to modulate fluid flow—such as a pump or a valve microchannel to control microcirculation within the chip.

Cells and tissues on the chip can be oxygenated using, for example, gas exchange membranes.

The chip can further comprise one or more sensors for monitoring a variable and/or a response of a cell to its surrounding conditions.

The chip can be fabricated from any suitable material that will be familiar to the person skilled in the art. Examples of such materials, suitably, biocompatible materials, are silicon, polyurethanes, glass, plastic, polymethylmethacrylate (PMMA), polycarbonate, polytetrafluoroethylene (TEFLON™), polyvinylchloride (PVC), polydimethylsiloxane (PDMS), and rubber.

The chip can also comprise further components, as required, such as oxygenators, pumps, valves, gas-exchangers and bubble traps.

Various kinds of organ-on-a-chip are described in the art—see for example, *Lab Chip* (2015) 15, 2688-2699 and *Lab. Chip* (2013) 13, 3538.

The function of tissue or organs on the chip can be assessed using various methods, some of which are described herein. For example the tissue or organs can be monitored morphologically using imagining techniques. The functionality of a lung chip can be monitored by measuring permeability barrier function, surfactant production, and measuring responses to cytokines, for example. The functionality of a liver chip can be monitored using various assays, at least some of which are described herein. Such assays can include transporter function, cytochrome P450 expression and albumin secretion.

Liver Based 3-Dimensional Culture

The liver plays a central role in detoxification, metabolism of carbohydrates, lipids and proteins as well as biotransformation of endogenous and exogenous substances. Liver functionality is closely linked to the assembly of highly specialised cells, the majority of which are hepatocytes, embedded in a complex 3-dimensional structure made up of so-called lobules. Biotransformation of compounds usually results in non-toxic and more soluble metabolites, however, occasionally, more toxic metabolites may be formed causing hepatotoxicity.

It is possible to culture 3-dimensional liver cells using various methods that are well documented in the art, including the use of collagen sandwich cultures, membrane bioreactors, stirrer bioreactors, hanging drop, polystyrene scaffold culture and using a microfluidic device.

Hepatocytes can be changed into 3-dimensions via various methods, including the use of sandwich culture, solid scaffold materials—such as polystyrene scaffolds, hydrogels—such as collagen type-I, or self-assembling of hepatocytes into spheroids.

Whilst the use of freshly isolated primary human hepatocytes limited may be the preferred lung cell type of the present disclosure, their availability is limited. Other choices of human liver cell lines include HepG2 and Hep2/C3A. A particularly suitable cell source is the HepaRG cell line. Other sources of human hepatocytes are human embryonic stem cell (hESC) derived hepatocytes and hepatocytes derived from induced pluripotent stem cells (iPSC).

3-dimensional liver spheroids are of particular use in the present disclosure. They can be produced in scaffold free systems in multiwell plates by the self-assembling of hepatocytes into aggregates or in stirrer bioreactors. Liver spheroids form liver like structures within and are viable for long periods of time exhibiting good functionality making them well suited for high throughput applications and for use on chips.

Lung Based 3-Dimensional Culture

As the morphology of the respiratory tract changes from the upper to the lower airways, many different cell culture models have been established using primary cells or cell lines and are contemplated for use in the present disclosure. The choice of exactly which cell or cell line to use will depend on the area of interest of the respiratory tract for a given study.

Lung-on-a-chip models are able to reproduce the structure and function of the living lung. In one example of such a model, a microfluidic system containing two closely apposed microchannels separated by a membrane can be fabricated. The membrane can be coated with extracellular matrix, and human alveolar epithelial cells and human pulmonary microvascular endothelial cells can be cultured on opposite sides of the membrane. Once the cells are grown to confluence, air is introduced into the epithelial compartment to create an air-liquid interface to mimic the lining of the alveolar air space.

Since the lung surface is exposed to air, the cell model is cultured at the air-liquid interface to mimic the lung more realistically.

Screening

The effect of one or more agents on 3-dimensional cells, tissues or organs can be determined using the methods described herein. In one aspect, there is described an in vitro method for assessing the response of a 3-dimensional cell, tissue or organ to an agent, the method comprising: (i) contacting a 3-dimensional cell or a co-culture or a 3-dimensional organ culture system or a 3-dimensional multi-organ culture system with at least one agent; and (ii) measuring one or more responses after contact with the at least one agent; wherein a difference in the one or more responses before and after contact with the at least one agent is indicative that the agent modulates the response of the cell, tissue or organ.

There is also described an in vitro method for assessing the response of a 3-dimensional liver cell, tissue or organ and a 3-dimensional lung cell, tissue or organ to an agent, the method comprising: (i) contacting a co-culture, or a 3-dimensional organ culture system, or a 3-dimensional multi-organ culture system with at least one agent; and (ii) measuring one or more responses after contact with the at least one agent; wherein a difference in the one or more responses before and after contact with the at least one agent is indicative that the agent modulates the response of the cell, tissue or organ.

Suitably, the penetration of at least one agent into the 3-dimensional lung cell, tissue or organ is measured or determined. Suitably, the bio-activation of the at least one agent in the 3-dimensional liver cell, tissue or organ is measured or determined. These steps can be carried out simultaneously or subsequently to each other.

The effect of one or more agents on 3-dimensional lung cell, tissue or organ can be determined using the methods described herein. The effect of one or more agents on 3-dimensional liver cell, tissue or organ can be determined using the methods described herein. The effect of one or more agents on 3-dimensional lung cell, tissue or organ and 3-dimensional liver cell, tissue or organ can be determined using the methods described herein. The effect of one or more agents on the penetration of an agent—such as an aerosol—into 3-dimensional lung cell, tissue or organ and its further bio-activation in liver cell, tissue or organ can be determined using the methods described herein. The agent can include, but is not limited to, a drug, a toxin, a pathogen, an antigen, an antibody, and an aerosol etc. The agent can be added to the 3-dimensional culture system described herein and its effect on the 3-dimensional cultured cell, tissue or organ can be monitored or determined. Examples of the effects that can be measured include consumption of oxygen, production of carbon dioxide, cell viability, expression of a protein, the activity of an enzyme, penetration, permeability barrier function, surfactant production, response to cytokines, transporter function, cytochrome P450 expression, albumin secretion and the like.

A plurality of assays may be run in parallel with different concentrations of the agent to obtain a differential response to the various concentrations. As known in the art, the process of determining the effective concentration of an agent typically uses a range of concentrations resulting from 1:10, or other log scale, dilutions. The concentrations may be further refined with a second series of dilutions, if necessary. Typically, one of these concentrations serves as a negative control.

An agent (for example, a test compound) may be any compound of interest and includes small organic compounds, polypeptides, peptides, higher molecular weight carbohydrates, polynucleotides, fatty acids and lipids, aerosol or one or more components of an aerosol and the like. Test compounds may be screened individually or in sets or combinatorial libraries of compounds. Test compounds can be obtained from a wide variety of sources including libraries of synthetic or natural compounds. Libraries of natural compounds in the form of bacterial, fungal, plant and animal extracts can be used. Natural or synthetically produced libraries and compounds that are modified through conventional chemical, physical and biochemical means may be used to produce combinatorial libraries. Known pharmacological agents may be subjected to directed or random chemical modifications, such as acylation, alkylation, esterification, acidification to produce structural analogues for screening. When screening using a combinatorial library, a large library of chemically similar or diverse molecules can be screened. In combinatorial screening, the number of hits discovered is proportional to the number of molecules tested. The large numbers of compounds, which may reach thousands of compounds tested per day, can be screened, in which laboratory automation and robotics may be applied. Many examples of methods for the synthesis of molecular libraries can be found in the art. A small organic compound includes a compound of molecular weight less than about 5000, usually less than about 2500, usually, less than about 2000, more usually, less than about 1500, suitably about 100 to about 1000. The small organic compounds may be either biological or synthetic organic compounds. The atoms present in the small organic compound are generally in the group comprising carbon, hydrogen, oxygen, and nitrogen and may include halogens, boron, phosphorus, selenium and sulphur if in a pharmaceutically acceptable form. Generally, oxygen, nitrogen, sulphur or phosphorus, if present, are bound to carbon or one or more of each other or to hydrogen to form various functional groups such as, for example, carboxylic acids, alcohols, thiols, carboxamides, carbamates, carboxylic acid esters, amides, ethers, thioethers, thioesters, phosphates, phosphonates, olefins, ketones, amines, aldehydes, and the like. The small organic compounds, as the term is used herein, also include small peptides, small oligonucleotides, small polysaccharides, fatty acids, lipids, and the like having a molecular weight less than about 5000.

Examples of pharmaceutical agents are described in The Pharmacological Basis of Therapeutics, Goodman and Gilman, McGraw-Hill, New York, N.Y., (1996), Ninth edition. The agent can be a toxin.

Test compounds in solution and solid samples that can be dissolved in a suitable solvent can be assayed. Test compounds in gaseous form can also be assayed by exposing samples to the gas for a period of time. Samples of interest include environmental samples, biological samples, manufacturing samples, libraries of compounds and synthetic and naturally occurring compounds.

Polypeptides that have a molecular weight of at least about 5,000, more usually at least about 10,000 can be screened. The test polypeptides will generally be from about 5,000 to about 5,000,000 or more molecular weight, more usually from about 20,000 to about 1,000,000 molecular weight. A wide variety of polypeptides may be considered such as a family of polypeptides having similar structural features, polypeptides having particular biological functions, polypeptides related to specific microorganisms, particularly disease causing microorganisms. Such polypeptides include cytokines or interleukins, enzymes, protamines, histones, albumins, immunoglobulins, scleropolypeptides, phosphopolypeptides, mucopolypeptides, chromopolypeptides, lipopolypeptides, nucleopolypeptides, glycopolypeptides, T-cell receptors, proteoglycans, somatotropin, prolactin, insulin, pepsin, polypeptides found in human plasma, blood clotting factors, blood typing factors, polypeptide hormones, cancer antigens, tissue specific antigens, peptide hormones, nutritional markers, tissue specific antigens, and synthetic peptides, which may or may not be glycated.

Polynucleotides can be screened. The test polynucleotide may be a natural compound or a synthetic compound. Polynucleotides include oligonucleotides and are comprised of natural nucleotides such as ribonucleotides and deoxyribonucleotides and their derivatives although unnatural nucleotide mimetics such as 2'-modified nucleosides, peptide nucleic acids and oligomeric nucleoside phosphonates are also contemplated. The higher molecular weight polynucleotides can have from about 20 to about 5,000,000 or more nucleotides.

One or more variables that can be measured include quantifiable elements of cells, subcellular material, subcellular components, or cellular products, particularly elements that can be accurately measured in a high throughput assay system. An output can be a feature, condition, state or function of any cell, cellular component or cellular product including viability, respiration, metabolism, cell surface determinant, receptor, protein or conformational or post-translational modification thereof, lipid, carbohydrate, organic or inorganic molecule, DNA, RNA and the like or a portion derived from such a cell component. While the variable(s) can provide a quantitative readout, in some instances a semi-quantitative or qualitative result can be obtained. Readout variables may include a single value, or a mean value, or a median value or a variance thereof, for example.

Various methods can be used to measure the variable(s) to determine the cell, tissue or organ's response to an agent/test compound. For measuring the amount of a molecule that is present, one method is to label the molecule with a detectable moiety, which may be fluorescent, luminescent, radioactive, enzymatically active, and the like. Fluorescent and luminescent moieties are available for labelling a biomolecule, structure, or cell type. Immunofluorescent moieties can be directed to bind not only to specific proteins but also specific conformations, cleavage products, or site modifications like phosphorylation. Individual peptides and proteins can be engineered to auto-fluoresce. Immunoassay techniques—such as immunohistochemistry, radioimmunoassay (RIA), or enzyme linked immunosorbance assay (ELISA) and related non-enzymatic techniques can be used. These techniques utilize specific antibodies as reporter molecules which are particularly useful due to their high degree of specificity for attaching to a single molecular target. Cell-based ELISA or related non-enzymatic or fluorescence-based methods enable measurement of cell surface parameters.

The results of screening assays may be compared to results obtained from reference compounds, concentration curves, controls and the like. The agent can be an aerosol—such as smoke or an aerosol derived from smoke.

Aerosol

One embodiment relates to studying the penetration of an agent—such as an aerosol—into the 3-dimensional lung cell, tissue or organ described herein. Another embodiment relates to studying the penetration of an agent—such as an aerosol—into the 3-dimensional lung cell, tissue or organ and its further bio-activation in liver cell, tissue or organ. In particular, this can be carried out on the 3-dimensional organ culture systems described herein.

The aerosol may be derived or generated by an aerosol forming device. Smoking articles and smokable articles are types of aerosol forming devices. Examples of smoking articles or smokable articles include but are not limited to cigarettes, cigarillos, and cigars. In certain aerosol forming devices, rather than combustion, a tobacco composition or another aerosol forming material is heated by one or more electrical heating elements to produce an aerosol. In another type of heated aerosol forming device, an aerosol is produced by the transfer of heat from a combustible fuel element or heat source to a physically separate aerosol forming material, which may be located within, around or downstream of the heat source. Typically in heated smoking articles, an aerosol is generated by the transfer of heat from a heat source to a physically separate aerosol-forming substrate or material, which may be located within, around or downstream of the heat source. During smoking, volatile compounds are released from the aerosol-forming material by heat transfer from the heat source and entrained in air drawn through the smoking article. As the released compounds cool, they condense to form an aerosol that is inhaled by the user. As used herein, the term 'aerosol forming material' is used to describe a material capable of releasing upon heating volatile compounds, which can form an aerosol. The aerosol forming material may be plant-based. Examples of aerosol forming materials include but are not limited to tobacco compositions, tobaccos, tobacco extract, cut tobacco, cut filler, cured tobacco, expanded tobacco, homogenized tobacco, reconstituted tobacco, and pipe tobaccos. The aerosol-forming material may alternatively comprise a non-plant-based-containing material.

The aerosol can be in the form of smoke. As used herein, the term 'smoke' is used to describe a type of aerosol that is produced by smoking articles, such as cigarettes, or by combusting an aerosol forming material. Smoke includes various agents, which can be provided as individual compounds for study if required. Examples of such agents include nicotine-free dry particulate matter, carbon monoxide, formaldehyde, acetaldehyde, acetone, acrolein, propionaldehyde, crotonaldehyde, methyl-ethly ketone, butyraldehyde, benzo[a]pyrene, phenol, m-cresol, o-cresol, p-cresol, catechol, resorcinol, hydroquinone, 1,3-butadiene, isoprene, acrylonitrile, benzene, toluene, pyridine, quinoline, styrene, N'-nitrosonornicotine (NNN), N'-nitrosoanatabine (NAT), N'-nitrosoanabasine (NAB), 4-(methylnitrosamino)-1-(3-pyridyl)-1-butanone (NNK), 1-aminonaphthalene, 2-aminonaphthalene, 3-aminobiphenyl, 4-aminobiphenyl, nitrogen monoxide (NO), nitrous oxide (NOx), cyanhydric acid, ammonia, arsenic, cadmium, chrome, lead, nickel, selenium and mercury.

The 3-dimensional organ culture system described herein can be exposed for various amounts of time to smoke. Smoke can be delivered using a Vitrocell smoking robot as described in *Am. J. Physiol. Lung Cell Mol Physiol* 304: L489-L503 (2013). A defined number of puffs per cigarette and a defined number of puffs per minute of exposure can be used and the number of cigarettes varied to adjust to the exposure times. Reference cigarettes—such as the reference cigarettes 3R4F can be used as the source of the smoke and smoked on the smoking robot in basic conformity with the International Organization for Standardization smoking regimen (ISO 2000). After exposure, the 3-dimensional organ culture system can optionally be incubated with fresh culture medium before analysis.

Kits

Kits are also contemplated. The culture medium or culture media described herein can be filled into one or more suitable containers. A suitable container can be a sterilisable flask or a sterilisable bottle or a sterilisable beaker comprising a top—such as a sealable or re-sealable top. Therefore, the present disclosure also relates to a container comprising the culture medium described herein. The present disclosure also relates to multiple containers comprising the culture media described herein. In addition, the present disclosure relates to a package or kit comprising single or multiple flasks or bottles comprising the culture media optionally together with instructions for preparing same. Optionally one or more of the cell types described herein can be included in the package or kit. Optionally one or more reference cigarettes can be included in the package or kit. Instructions for use can also be included.

Further Aspects

Further aspects of the disclosure are presented in the following numbered paragraphs:

1. An isolated 3-dimensional liver spheroid, wherein the spheroid has: increased ATP content as compared to a 3-dimensional liver spheroid cultured in Complete William's E medium alone; the same or increased activity of cytochrome P450 1A1 and cytochrome P450 1B1 as compared to a 3-dimensional liver spheroid cultured in Complete William's E medium alone; and increased albumin secretion as compared to a 3-dimensional liver spheroid cultured in William's E medium alone.

2. An isolated 3-dimensional liver spheroid for use in a 3-dimensional multi-organ culture system obtained or obtainable by a process comprising: culturing a 3-dimensional liver spheroid in a cell culture medium comprising or consisting or consisting essentially of either: (a) Complete PneumaCult-ALI medium; or (b) Complete B-ALI medium; or (c) Complete PneumaCult-ALI medium and Complete William's E medium, or (d) Complete B-ALI medium and Complete William's E medium, for a period of time that is sufficient to obtain a 3-dimensional liver spheroid in which: ATP content is increased as compared to a 3-dimensional liver spheroid cultured in Complete William's E medium alone; cytochrome P450 1A1 and cytochrome P450 1B1 activity is increased as compared to a 3-dimensional liver spheroid cultured in Complete William's E medium alone; and albumin secretion is increased as compared to a 3-dimensional liver spheroid cultured in Complete William's E medium alone.

3. The isolated 3-dimensional liver spheroid according to paragraph 1 or paragraph 2 wherein the spheroid is or is derived from a human hepatic progenitor cell line, suitably, wherein the spheroid is or is derived from a HepaRG cell.

4. The isolated 3-dimensional liver spheroid according to paragraph 1 or paragraph 3, wherein the spheroid is cultured in a cell culture medium comprising or consisting or consisting essentially of either: (a) Complete PneumaCult-ALI medium; or (b) Complete B-ALI medium; (c) Complete PneumaCult-ALI medium and Complete William's E medium, or (d) Complete B-ALI medium and Complete William's E medium.

5. A co-culture comprising the 3-dimensional liver spheroid according to any of the preceding paragraphs and a 3-dimensional lung epithelial cell.

6. The co-culture according to paragraph 5, wherein the co-culture is maintained in a cell culture medium comprising or consisting or consisting essentially of either: (a) Complete PneumaCult-ALI medium; or (b) Complete B-ALI medium; or (c) Complete PneumaCult-ALI medium and Complete William's E medium, or (d) Complete B-ALI medium and Complete William's E medium.

7. A 3-dimensional organ culture system comprising the isolated 3-dimensional liver spheroid according to any of paragraphs 1 to 4.

8. A 3-dimensional multi-organ culture system comprising the isolated 3-dimensional liver spheroid according to any of paragraphs 1 to 4 and further comprising at least one other 3-dimensional cell type, or comprising the co-culture according to paragraph 5 or paragraph 6.

9. The 3-dimensional organ culture system according to paragraph 7 or the 3-dimensional multi-organ culture system according to paragraph 8, wherein the 3-dimensional liver spheroid is submerged in culture medium contained on the culture system.

10. The 3-dimensional multi-organ culture system according to paragraph 8 or 9, further comprising a 3-dimensional lung epithelial cell, suitably, wherein the 3-dimensional lung epithelial cell is at an air liquid interface on the 3-dimensional multi-organ culture system.

11. A 3-dimensional multi-organ culture system comprising: (a) a first organ growth section comprising a first organ cavity adapted to submerge a first 3-dimensional cell type in a culture medium; (b) a second organ growth section comprising a second organ cavity adapted to culture a second 3-dimensional cell type at an air liquid interface, the second 3-dimensional cell type being a cell type that is different than the first 3-dimensional cell type; and (c) a culture medium reservoir connecting the first organ cavity and the second organ cavity to allow for the flow of culture medium there between.

12. The 3-dimensional multi-organ culture system according to paragraph 11, wherein the first organ cavity and second organ cavity contain the same culture medium.

13. The 3-dimensional multi-organ culture system according to paragraph 11 or paragraph 12, comprising the co-culture according to paragraph 5 or paragraph 6.

14. The 3-dimensional organ culture system according to paragraph 7 or the 3-dimensional multi-organ culture system according to any of paragraphs 8 to 13, wherein said system is miniaturised.

15. The 3-dimensional organ culture system according to paragraph 7 or 14, or the 3-dimensional multi-organ culture system according to any of paragraphs 8 to 14, wherein said system comprises or is a microfluidic device, suitably, wherein said system is an organ-on-a-chip.

16. A cell culture medium comprising or consisting or consisting essentially of: (a) a mixture of Complete PneumaCult-ALI medium and Complete William's E medium; or (b) a mixture of Complete B-ALI medium and Complete William's E medium.

17. The cell culture medium according to paragraph 16, further comprising the 3-dimensional liver spheroid according to any of paragraphs 1 to 4 or the co-culture according to paragraph 5 or paragraph 6.

18. A 3-dimensional multi-organ culture system comprising a culture medium, said culture medium selected from the group consisting of a culture medium comprising or consisting or consisting essentially of either: (a) Complete PneumaCult-ALI medium; or (b) Complete B-ALI medium; or (c) Complete PneumaCult-ALI medium and Complete William's E medium, or (d) Complete B-ALI medium and Complete William's E medium or a combination of two or more thereof.

19. A method of preparing a 3-dimensional liver spheroid for use in a 3-dimensional organ culture system comprising: (i) providing a 3-dimensional liver spheroid; (ii) contacting the 3-dimensional liver spheroid with a culture medium comprising or consisting or consisting essentially of either: (a) Complete PneumaCult-ALI medium; or (b) Complete B-ALI medium; or (c) Complete PneumaCult-ALI medium and Complete William's E medium, or (d) Complete B-ALI medium and Complete William's E medium; and (iii) obtaining a 3-dimensional liver spheroid for use in a 3-dimensional organ culture system.

20. A method of preparing a co-culture comprising or consisting or consisting essentially of a 3-dimensional liver spheroid and a 3-dimensional lung epithelial cell for use in a 3-dimensional multi-organ culture system comprising: (i) providing a 3-dimensional liver spheroid and a 3-dimensional lung epithelial cell; (ii) contacting the 3-dimensional liver spheroid and the 3-dimensional lung epithelial cell with a culture medium comprising or consisting or consisting essentially of either: (a) Complete PneumaCult-ALI medium; or (b) Complete B-ALI medium; or (c) Complete PneumaCult-ALI medium and Complete William's E medium, or (d) Complete B-ALI medium and Complete William's E medium; and (iii) obtaining a co-culture of a 3-dimensional liver spheroid and a 3-dimensional lung epithelial cell.

21. An in vitro method for assessing the response of a 3-dimensional liver spheroid to an agent, the method comprising: (i) contacting the 3-dimensional liver spheroid according to any of paragraphs 1 to 4 or the co-culture according to paragraph 5 or 6 or the 3-dimensional organ culture system according to paragraph 7, 14 or 15, or the 3-dimensional multi-organ culture system according to any of paragraphs 8 to 15 with at least one agent; and (ii) measuring one or more responses of the 3-dimensional liver spheroid or the co-culture or the 3-dimensional organ culture system or the 3-dimensional multi-organ culture system after contact with the at least one agent; wherein a difference in the one or more responses before and after contact with the at least one agent is indicative that the agent modulates the response of the cell.

22. An in vitro method for assessing the response of a 3-dimensional liver spheroid and a 3-dimensional lung epithelial cell to an agent, the method comprising: (i) contacting the co-culture according to paragraph 5 or 6 or the 3-dimensional organ culture system according to paragraph 7, 14 or 15, or the 3-dimensional multi-organ culture system according to any of paragraphs 8 to 15 with at least one agent; and (ii) measuring one or more responses of the co-culture or the 3-dimensional organ culture system or the 3-dimensional multi-organ culture system after contact with the at least one agent; wherein a difference in the one or more responses before and after contact with the at least one agent is indicative that the agent modulates the response of the cell.

23. The in vitro method according to paragraph 22, wherein step (ii) comprises measuring the penetration of the at least one agent into the 3-dimensional lung epithelial cell.

24. The in vitro method according to paragraph 23, comprising the further step of: (iii) measuring the bio-activation of the at least one agent in the 3-dimensional liver spheroid; wherein the measurements in steps (ii) and (iii) are carried out simultaneously or wherein the measurement in step (iii) is carried out after the measurement in step (ii).

25. The in vitro method according to any of paragraphs 22 to 24, wherein the agent is an aerosol, suitably, wherein the aerosol is or is derived from smoke, suitably, cigarette smoke.

26. Use of a cell culture medium comprising or consisting or consisting essentially of either: (a) Complete PneumaCult-ALI medium; or (b) Complete B-ALI medium; or (c) Complete PneumaCult-ALI medium and Complete William's E medium, or (d) Complete B-ALI medium and Complete William's E medium, for culturing a 3-dimensional liver spheroid or a 3-dimensional lung epithelial cell or for co-culturing a 3-dimensional liver spheroid and a 3-dimensional lung epithelial cell.

27. Use of the 3-dimensional organ culture system according to paragraph 7, 14 or 15, or the 3-dimensional multi-organ culture system according to any of paragraphs 8 to 15 for toxicity testing or for drug discovery or for determining the penetration of an agent into lung cells and/or for determining the bio-activation of an agent in liver cells, suitably, wherein the agent is an aerosol.

Although illustrative embodiments of the invention have been disclosed in detail herein, with reference to the accompanying drawings, it is understood that the invention is not limited to the precise embodiment and that various changes and modifications can be effected therein by one skilled in the art without departing from the scope of the invention as defined by the appended claims and their equivalents.

The invention is further described in the Examples below, which are provided to describe the invention in further detail. These examples, which set forth a preferred mode presently contemplated for carrying out the invention, are intended to illustrate and not to limit the invention.

EXAMPLES

Example 1

Preparation of Bronchial Organotypic Cultures

These are prepared according to the protocol from Lonza (Basel, Switzerland) entitled Clonetics™ B-ALI™ air-liquid interface medium. Briefly, normal human bronchial epithelial cells (NHBEC) are expanded in Complete B-ALI medium at 37° C. in 5% CO2 (90% relative humidity) until a confluency of approx. 80%. Cells are trypsinized, washed and resuspended. 35,000 cells are seeded onto collagen-I-coated Transwell® inserts (Corning®, Root Langenbold, Switzerland), and inserts are placed in multiwell plates prefilled with Complete B-ALI medium (Lonza) and incubated for 3 days. Apical medium is then removed, and basal medium is replaced with Complete B-ALI medium. Air-lifted inserts are returned to the incubator, and medium is replaced every 2 to 3 days. Additionally, apical washes are performed once a week during the maturation phase. Cultures are used once mature, typically at 4 weeks following the air-lift. Morphological assessment, measurements of ATP content, apical ATP secretion and CYP1A1/B1 activity are performed weekly, for up to 4 weeks after maturation (see FIG. 1). With the exception of inserts dedicated to histological evaluation and ATP content measurements, all inserts are re-used throughout the time course.

Example 2

Preparation of Liver Spheroids

Liver spheroids are prepared as described in the GravityTRAP™ ULA Plate manual from InSphero. Briefly, HepaRG cells are first thawed at 37° C. for 2 minutes and then mixed into 9 ml of pre-warmed William's E medium (ThermoFisher Scientific, ref. 12551032) supplemented with Thaw, Plate & General Purpose supplement (ThermoFisher Scientific, ref. HPRG770) and GlutaMAX solution (ThermoFisher Scientific, ref. 35050061). Cells are then centrifuged for 2 minutes at 400×g before medium is replaced with fresh William's E medium with the same supplements as described above. About 5000 cells are then distributed per wells of a Corning® spheroid microplate (ref. 4520). 5 days later, medium is replaced with fresh William's E medium (ThermoFisher Scientific, ref. 12551032) supplemented with HepaRG Maintenance & Metabolism Supplement (ThermoFisher Scientific, ref. HPRG720) and GlutaMAX solution (ThermoFisher Scientific, ref. 35050061). One week later, spheroids are mature and ready to be used for the experiments.

Example 3

Determining Morphology of Bronchial Organotypic Cultures and Liver Spheroids

Morphology of bronchial organotypic cultures is evaluated following fixation and paraffin embedding, sectioning and staining with hematoxylin and eosin (H&E) and Alcian blue as previously described in Toxicol Sci. 2015 September; 147(1):207-21.

Liver spheroid morphology is assessed following immunostaining. In brief, liver spheroids are fixed in 4% fresh paraformaldehyde overnight. Following blocking in 1% Triton X-100/0.2% fish skin gelatin (FSG), spheroids are stained with mouse anti-cytokeratin 19 (1/500, Abcam, Cambridge, UK) diluted in PBS with 0.1% FSG for 24 hours. The primary antibody is visualized using a FITC-labeled goat anti-mouse antibody (1/500, Abcam). Spheroids are then mounted using ProLong Diamond antifade with DAPI (Thermo Fisher) and evaluated by high-content imaging on the Cellinsight™ CX7 platform (Thermo Fisher).

Example 4

Determining ATP Content of Bronchial Organotypic Cultures and Liver Spheroids

This is determined using the CellTiterGlo® 3D cell viability assay (Promega, Dübendorf, Switzerland) according to the manufacturer's recommendations.

For measurements in bronchial cultures, undiluted CellTiterGlo® reagent is directly added to the cultures, yielding intracellular ATP content.

For analysis of liver spheroids, CellTiterGlo® reagent is first diluted in William's E medium (1:1 (v/v)) and then added to the wells of the spheroid plate. Therefore, ATP measurements in liver spheroids account for both intracellular and extracellular ATP content (i.e. total ATP). Luminescence is recorded using a FLUOstar Omega plate reader (BMG Labtech, Ortenberg, Germany) 30 minutes after addition of the CellTiterGlo® reagent.

Example 5

Determining ATP Secretion of Bronchial Organotypic Cultures and Liver Spheroids

ATP secretion into the airway surface liquid (ASL) of bronchial organotypic cultures is measured following addition of hypotonic (5.2 mM KCl, 1.2 mM $CaCl_2$, 1.2 mM $MgCl_2$, 10 mM glucose, 10 mM TES, pH 7.4) saline solution. In brief, cultures are first washed with PBS and then treated with isotonic saline for 5 minutes. The apical solution is then carefully collected. 60 minutes later, cultures are treated apically with hypotonic solution for 5 minutes, after which the apical solution is carefully collected. ATP content of the collected ASL samples is measured using the ENLITEN® ATP Assay System (Promega). Luminescence is recorded using a FLUOstar Omega plate reader (BMG Labtech). The ATP concentration is extrapolated from a standard curve.

Example 6

Gene Expression Analysis

RNA is prepared from lung and liver tissues using the miRNeasy Mini kit (QIAGEN, Hilden, Germany). cDNA is prepared using the RT2 First strand kit and mixed with $RT^2$ qPCR Mastermix prior to plating the mix on the Phase I Enzymes RT2 Profiler PCR Array (QIAGEN). qPCR is performed using the ViiA™ 7 Real-Time PCR System (Thermo Fisher), and data is analysed following the instructions provided by QIAGEN. Fold changes with an unadjusted p-value <0.05 (t-test) are considered statistically significant.

Example 7

Measuring Inducibility and Activity of CYP1A1/B1, CYP1A2, and CYP2B6 Enzymes

Metabolic capability of both culture systems is further confirmed by examining inducibility and activity of CYP1A1/B1, CYP1A2, and CYP2B6 enzymes using P450-Glo Assays (Promega) according to the manufacturer's instruction. CYP activities are induced 48 hours prior measurement with a combination of 10 nM Tetrachlorodibenzodioxin (TCDD) and 25 µM rifampicin (Sigma-Aldrich, Buchs, Switzerland). 20 µM α-naphthoflavone and 10 µM fluvoxamine maleate (Sigma) are used to inhibit CYP1A1/B1 and CYP2B6 activities, respectively. Once the measurements are completed, tissues are washed twice with PBS and returned to the incubator.

Example 8

Measuring Albumin Secretion

Albumin secretion by liver spheroids is quantified 48 hours after the last medium change using the Human Albumin ELISA kit (Abcam). The same cell culture supernatant is analyzed for release of α-GST using the Human α-GST ELISA kit (Wuhan EIAab, distributed by LuBioScience, Luzern, Switzerland).

Example 9

Measuring Cytotoxicity and Apoptosis

The ApoTox-Glo™ triplex assay (Promega, Dübendorf, Switzerland) is used to determine the number of damaged/necrotic and apoptotic cells. Cells are first incubated with bis-alanyl-alanyl-phenylalanyl-rhodamine 110 (bis-AAF- R110) for 30 minutes to quantify the number of damaged cells. Then, the same spheroids were incubated with a specific caspase 3/7 reagent to measure the number of apoptotic cells.

Example 10

Preparation of a Mixture of PneumaCult-ALI Medium and William's E Medium.

Complete PneumaCult-ALI medium is prepared by mixing PneumaCult-ALI Basal Medium (StemCell Technologies, ref. 05002) with PneumaCult-ALI 10× Supplement (StemCell Technologies, ref. 05003), PneumaCult-ALI Maintenance Supplement (StemCell Technologies, ref. 05006), Hydrocortisone Stock Solution (StemCell Technologies, ref. 07925) and 0.2% Heparin Sodium Salt in PBS (StemCell Technologies, ref. 37250).

William's E medium (ThermoFisher Scientific, ref. 12551032) is supplemented with HepaRG Maintenance & Metabolism Supplement (ThermoFisher Scientific, ref. HPRG720) and GlutaMAX solution (ThermoFisher Scientific, ref. 35050061) to give Complete William's E medium.

Complete PneumaCult-ALI medium is mixed with Complete William's E medium at varying percentages, giving mixtures ranging from 70/30 to 100/0% (v/v) complete PneumaCult-ALI medium/Complete William's E medium.

Example 11

Mixture of Complete B-ALI Medium and William's E Medium.

Complete William's E medium is prepared as outlined in Example 1.

Complete B-ALI medium is prepared by combining the ingredients of the B-ALI BulletKit™ (Lonza, ref. 193514). Complete B-ALI medium is mixed with Complete William's E medium in a percentage varying from 70 to 100% B-ALI medium. Complete B-ALI medium is mixed with Complete William's E medium at varying percentages, giving mixtures ranging from 70/30 to 100/0% (v/v) Complete PB-ALI medium/Complete William's E medium.

Example 12

Determining the Effects of Different Culture Media

The effects of the different media and their dilutions are assessed over a 9-day period by culturing the cells at 37° C. with 5% $CO_2$ and 90% of relative humidity.

The effects of the different media and their dilutions are assessed over a 9-day period. HepaRG cells are first seeded onto Corning® Spheroid Microplates using the William's E medium complemented with Thaw, Plate, & General Purpose Supplement (Thermo Fisher Scientific, ref. HPRG770) and GlutaMAX solution. After 1 week of maturation, medium is exchanged for a mixture of PneumaCult-ALI medium or B-ALI differentiation medium with William's E medium complemented with Maintenance & Metabolism Supplement. Percentage of Complete PneumaCult-ALI or B-ALI diluted in Complete William's E medium was 70%, 80%, 90% and 100%. 9 days later, spheroids are used for experiments. All the results obtained with the medium mixtures are compared to spheroids maintained with the Complete William's E medium only.

Example 13

Measuring Total Glutathione Levels

The GSH/GSSG-Glo assay (Promega, Dübendorf, Switzerland) is used to determine total glutathione levels as a marker of antioxidant capacity. In this assay, spheroids are incubated for 30 minutes with either a Total Glutathione Buffer (GSH+GSSG) or an Oxidized Glutathione Buffer (GSH). Following addition of a luciferin detection reagent, luminescence is measured with a FLUOstar Omega plate reader. As the assay allows to measure the total GSH+GSSG and GSSG, it is possible to deduce the GSH amount in the samples.

Example 14

The results of some of the experiments carried out are summarised in Table 1.

Example 15

ATP Content of Liver Spheroids

A significant ($P<0.05$) ATP increase in all the conditions is found when Complete Pneumacult-ALI medium or Complete B-ALI medium is used. The highest ATP content is seen when spheroids are maintained in 100% Complete Pneumacult-ALI medium with similar ATP content when using 70%, 80% and 90% Complete Pneumacult-ALI medium. ATP content of spheroids maintained in Complete B-ALI medium is always lower compared to that of spheroids cultured in Complete Pneumacult-ALI medium, and the lowest value is obtained for spheroids maintained in 100% of Complete B-ALI medium.

Example 16

Cytochrome P450 1A1 and Cytochrome P450 B1 Activity of Liver Spheroids

Activity of cytochrome P450 1A1 and cytochrome P450 B1 is significantly ($P<0.05$) increased in induced spheroids cultured in mixtures of Complete William's E medium and Complete B-ALI medium or in mixtures of Complete William's E medium and Complete Pneumacult medium. In induced spheroids maintained in 100% Complete B-ALI™ medium, cytochrome P450 1A1 and cytochrome P450 B1 activity is similar to that of spheroids cultured in Complete William's E medium. Basal cytochrome P450 1A1 and cytochrome P450 B1 activity is also significantly ($P<0.05$) higher in samples maintained with 70% & 80% of Complete Pneumacult-ALI or Complete B-ALI™ medium.

Example 17

Assessing the Number of Damaged/Necrotic Liver Spheroids

Aside from the 70% Complete Pneumacult-ALI condition, the 9-day incubation with the Complete William's E medium and Complete Pneumacult-ALI medium/Complete B-ALI medium mixtures, significantly ($P<0.005$) increases the number of damaged/necrotic cells in all conditions. Moreover, an increasing amount of Complete Pneumacult-ALI medium/Complete B-ALI medium results in an increase in the number of necrotic cells. The number of damaged/necrotic cells is significantly ($P<0.05$) higher when using the Complete B-ALI mixtures compared with the Complete Pneumacult-ALI mixtures (when comparing similar % of mixtures). Apart from the standard condition, the lowest number of necrotic cells was obtained with media mixtures containing 70% Complete Pneumacult-ALI.

All media mixtures significantly increase the number of apoptotic cells (P<0.05), with the highest numbers seen in spheroids cultured in Complete William's E-medium and Complete Pneumacult-ALI medium mixtures. The number of apoptotic cells in spheroids maintained in Complete William's E and Complete B-ALI medium mixtures is significantly (P<0.05) lower compared with the Complete William's medium and Complete Pneumacult-ALI medium mixtures for the 70%, 80% and 100% mixtures (when comparing similar % of mixtures). The condition allowing for the lowest number of apoptotic cells is obtained with 100% B-ALI medium.

Example 18

Glutathione (GSH) and Oxidised Glutathione (GSSG) Levels of Liver Spheroids

Culturing liver spheroids for 9 days in the various mixtures of Complete William's E medium and Complete Pneumacult-ALI medium/Complete B-ALI medium, the level of GSH is significantly (P<0.05) higher in cultures with 70% and 80% Complete Pneumacult-ALI medium compared to the Complete William's E medium. Higher amounts of Complete Pneumacult-ALI medium do not further increase GSH content, but decrease them. Similarly, GSH levels are significantly (P<0.05) higher in spheroids maintained in mixtures with 70% Complete B-ALI medium compared to Complete William's E medium alone. As with Complete Pneumacult-ALI medium, GSH content decreases with increasing amounts of Complete B-ALI medium, eventually (at 100% Complete B-ALI medium) reaching a value below that seen in spheroids cultured in William's E medium.

With the same assay, the GSSG content is also measured. GSSG is always significantly higher in liver spheroids maintained in mixtures of Complete William's E medium with Complete Pneumacult-ALI medium/Complete B-ALI medium compared to the 100% Complete William's E medium, independent of the type of Complete Pneumacult-ALI medium/Complete B-ALI medium used or its concentration. While the GSSG content is only slightly elevated in spheroids cultured in Complete William's E medium and Complete B-ALI medium mixtures above that of spheroids maintained in Complete William's E medium only, GSSG content is strongly increased in spheroids maintained with Complete William's E medium and Complete Pneumacult-ALI medium mixtures.

Example 19

Albumin Secretion of Liver Spheroids

While albumin secretion of spheroids maintained with Complete William's E medium is lower than the expected results (expected: 15-30 pg/day/cell; obtained: 4 pg/day/cell (Gunness et al., 2013)), a significant (P<0.05) increase in the release of albumin with all media mixtures tested is measured. Secreted albumin of spheroids maintained with 70%, 80% and 90% Complete William's E and Complete Pneumacult-ALI medium/Complete B-ALI medium is significantly (P<0.05) higher for spheroids maintained with Complete Pneumacult-ALI than with Complete B-ALI™ medium (when comparing same %).

Example 20

Gene Expression

Figure 7:
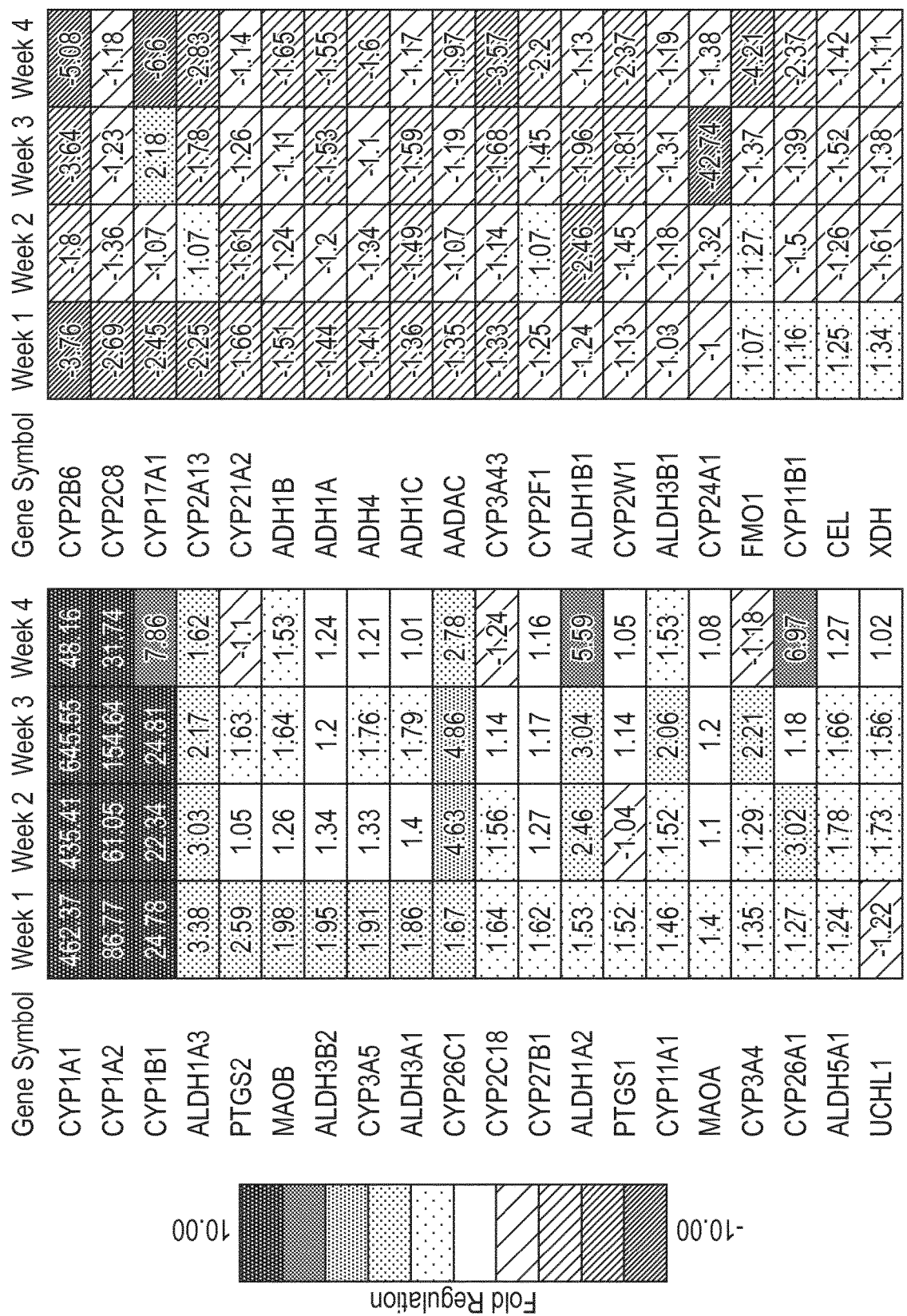
FIG. 7. Fold regulation of the expression of phase 1 drug metabolism enzyme-encoding genes in 3-dimensional organotypic lung cultures is assessed at 1, 2, 3, and 4 weeks. Gene expression is compared between lung cultures treated with TCDD and rifampicin for 48 hours (n=3) and untreated cultures (n=3), and fold changes are calculated using the ΔΔCT method. The heatmaps list the 20 most up—(in red, on the left) and down-regulated genes (in blue, on the right) together with the fold change. Gene symbols are displayed on the left side of the heatmaps.
Figure 8:
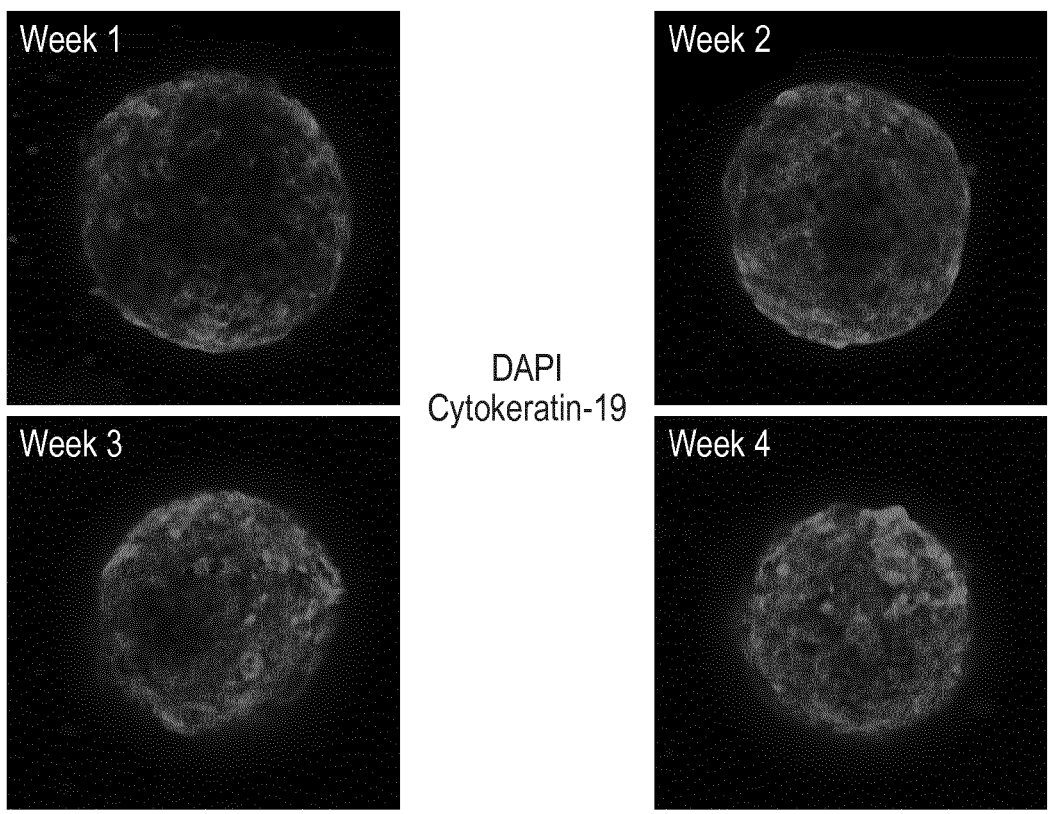
FIG. 8. Liver spheroids stained for cytokeratin 19 expression at 1, 2, 3, and 4 weeks following maturation. Shown are representative images in pseudocolors (CK19 in red, nuclei in blue) at 10× magnification.
Figure 9:
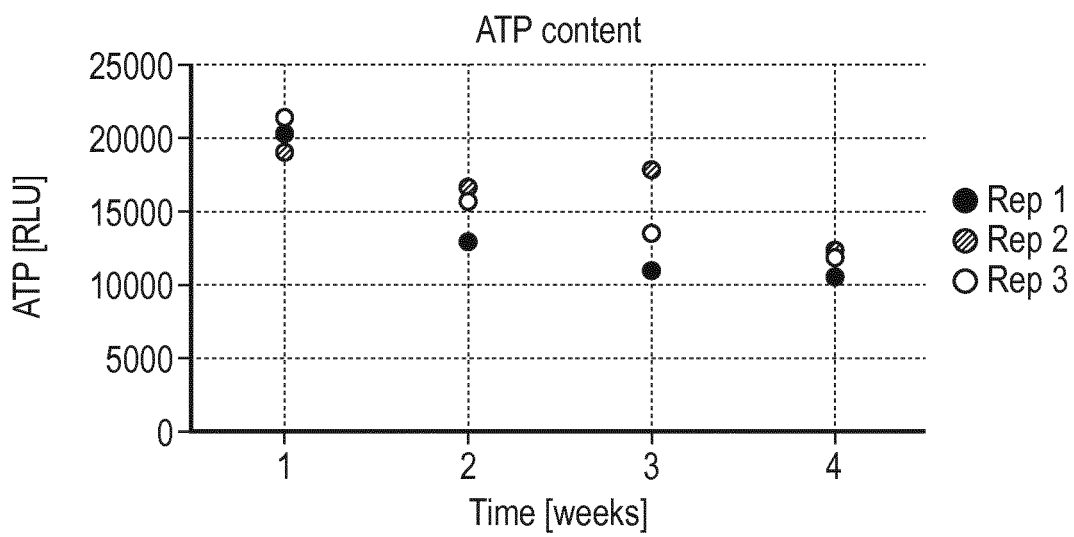
FIG. 9. Total ATP content of liver spheroids and their conditioned media is measured at 1, 2, 3, and 4 weeks following maturation. Results for 3 independent measurements are shown. Rep. Replicate FIG. 10. Albumin secretion from liver spheroids is quantified at 1, 2, 3, and 4 weeks following maturation Results for 8 independent measurements are shown. The dotted line indicates the trend based on the average value per time point. Rep: Replicate; Alpha-GST production by liver spheroids is assessed at 1, 2, 3, and 4 weeks following maturation. Results for 8 independent measurements are shown. Rep: Replicate; Cytochrome P450 1A1/B1 activity is measured in liver spheroids at 1, 2, 3, and 4 weeks following maturation. Results show basal CYP activity, induced activity following 48-h treatment with TCDD and rifampicin, and induced activity following inhibition with α-naphtoflavone. Results are presented as mean±SEM of 3 independent experiments; Cytochrome P450 1A2 activity is measured in liver spheroids at 1, 2, 3, and 4 weeks following maturation. Results show basal CYP activity, induced activity following 48-h induction with TCDD and rifampicin, and induced activity following inhibition with fluvoxamine maleate. Results are presented as mean±SEM of 3 independent experiments.
Figure 10:
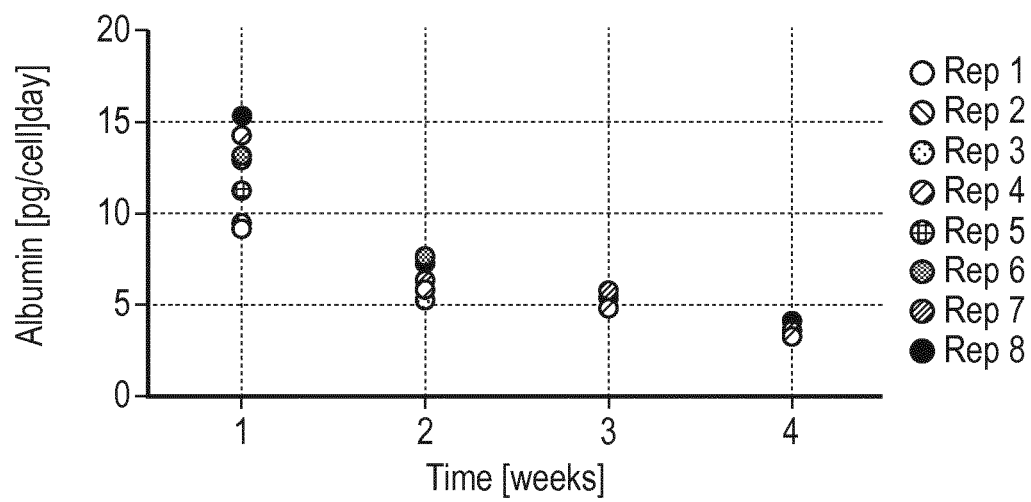
Figure 10:
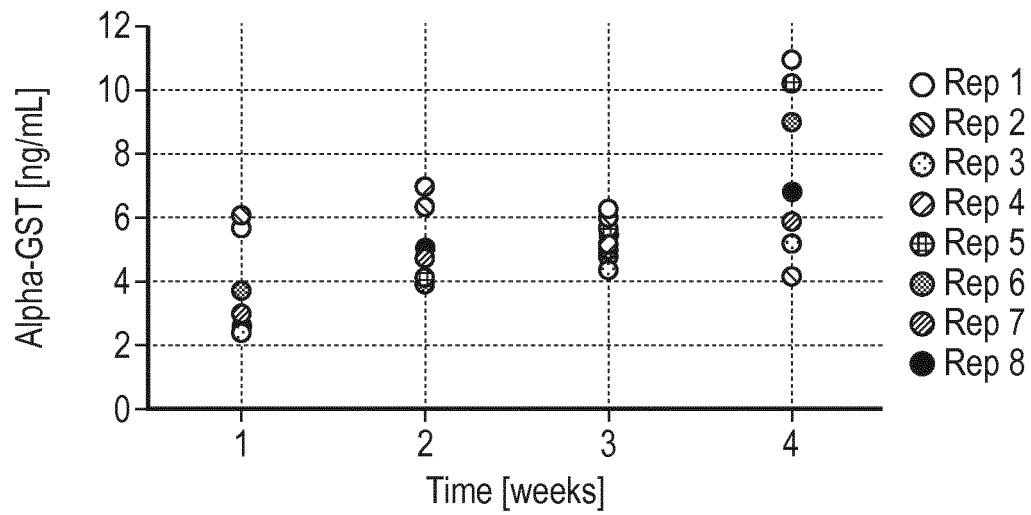
Figure 10:
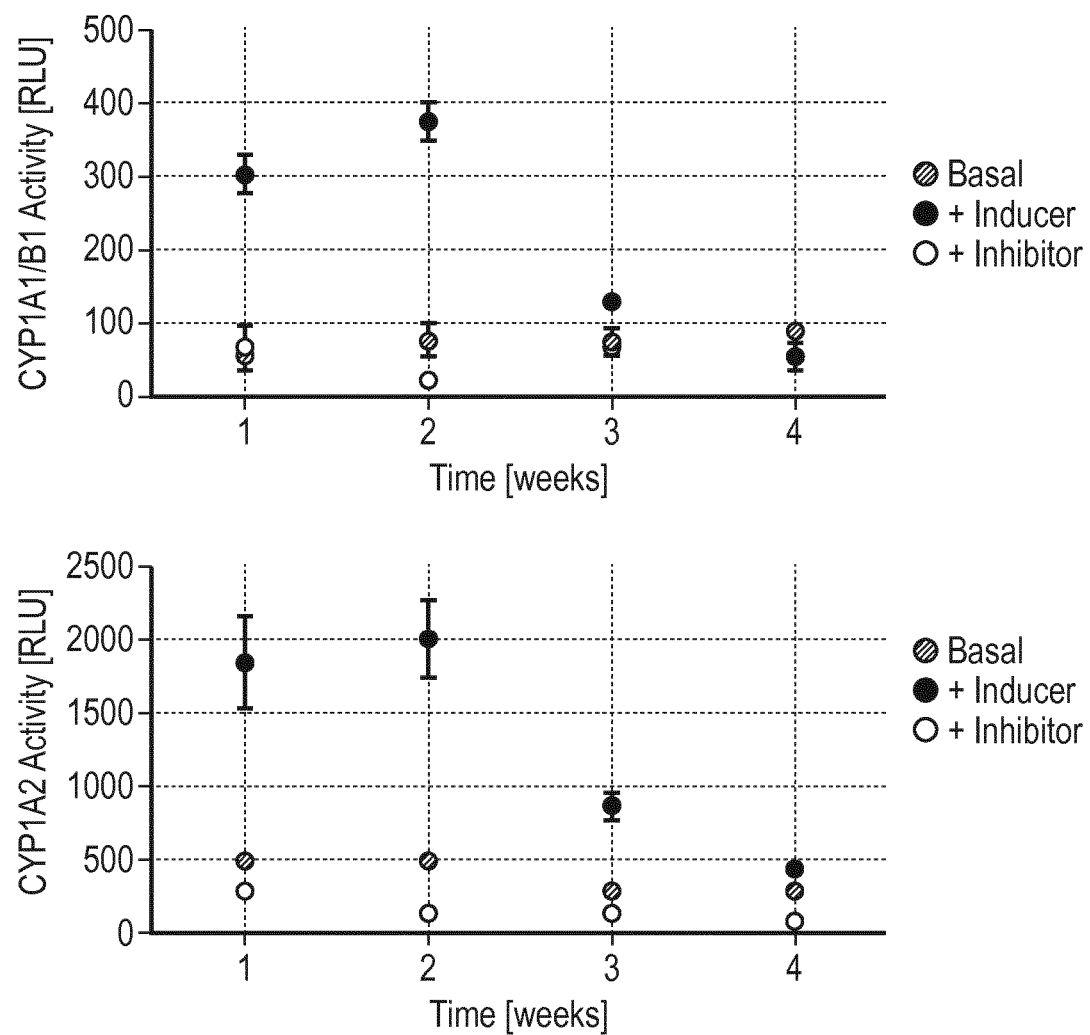
Figure 11:
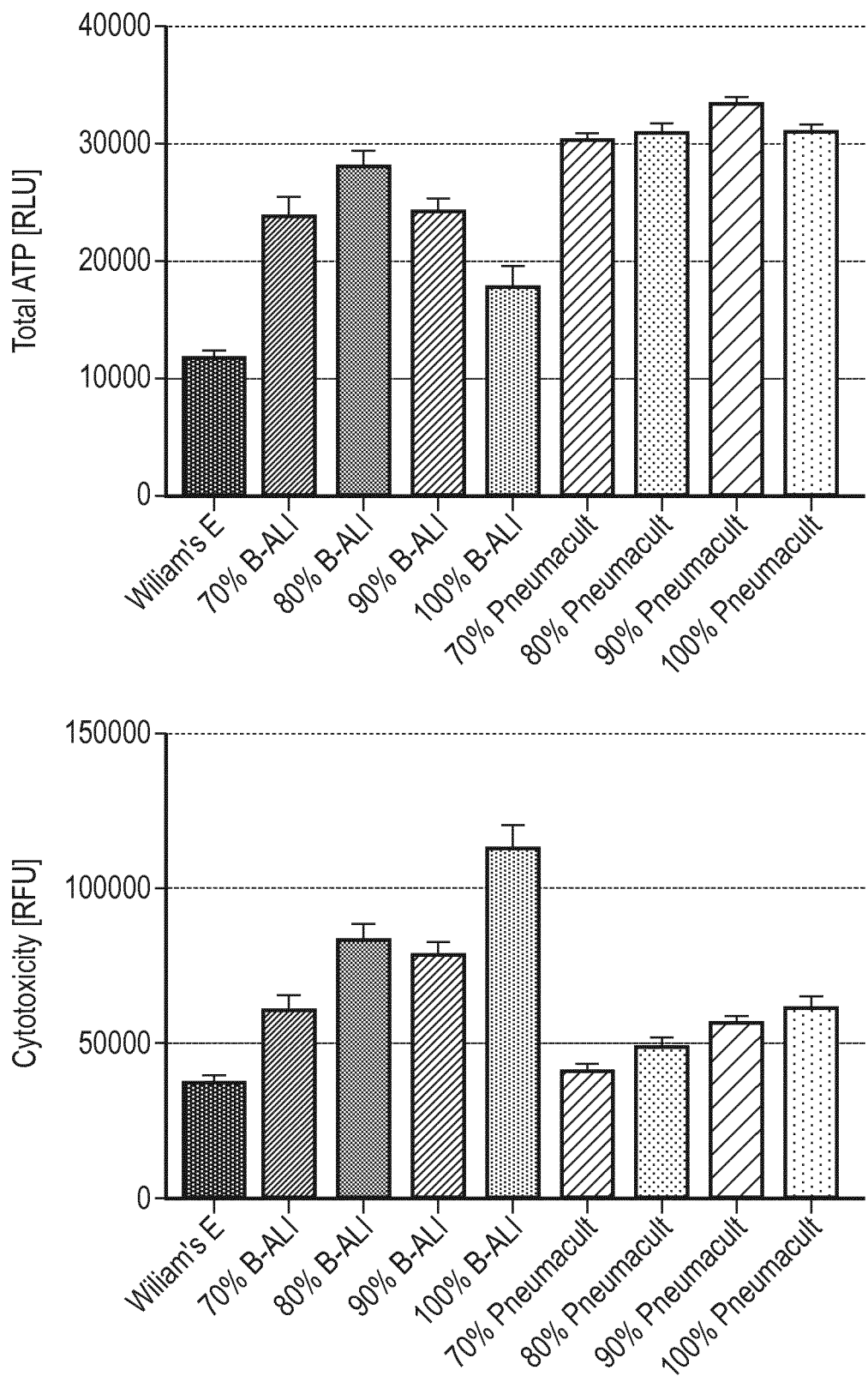
FIG. 11. Total ATP content of liver spheroids and their conditioned media is measured following culture in mixtures of William's E and Complete B-ALI medium or Complete PneumaCult-ALI medium (StemCell Technologies, Grenoble, France). Results are presented as mean±SEM for 5 independent measurements; Cytotoxicity is measured in liver spheroids following culture in mixtures of William's E and Complete B-ALI medium or Complete PneumaCult-ALI medium. Results are presented as mean±SEM for 5 independent measurements. RFU: Relative fluorescence units FIG. 12. Apoptosis is measured in liver spheroids following culture in mixtures of William's E and Complete B-ALI medium or Complete PneumaCult-ALI medium medium. Results are presented as mean±SEM for 5 independent measurements; CYP1A1/B1 activity is measured in liver spheroids following culture in mixtures of William's E and Complete B-ALI medium or Complete PneumaCult-ALI medium. Results are presented as mean±SEM for 3 independent measurements.
Figure 12:
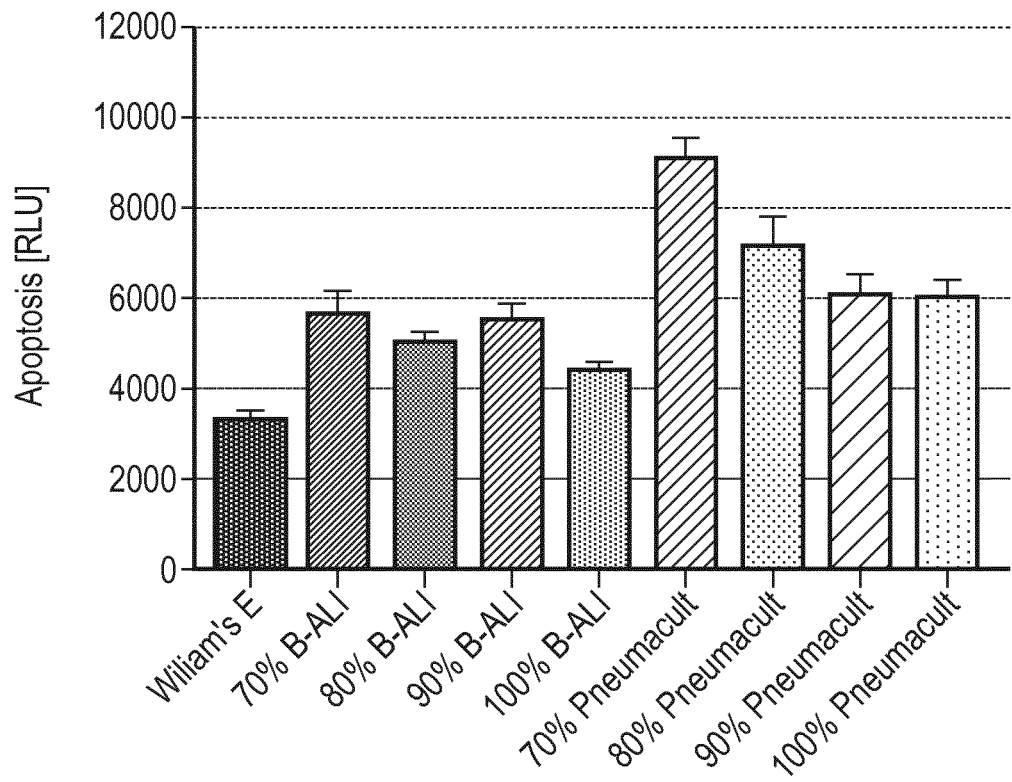
Figure 12:
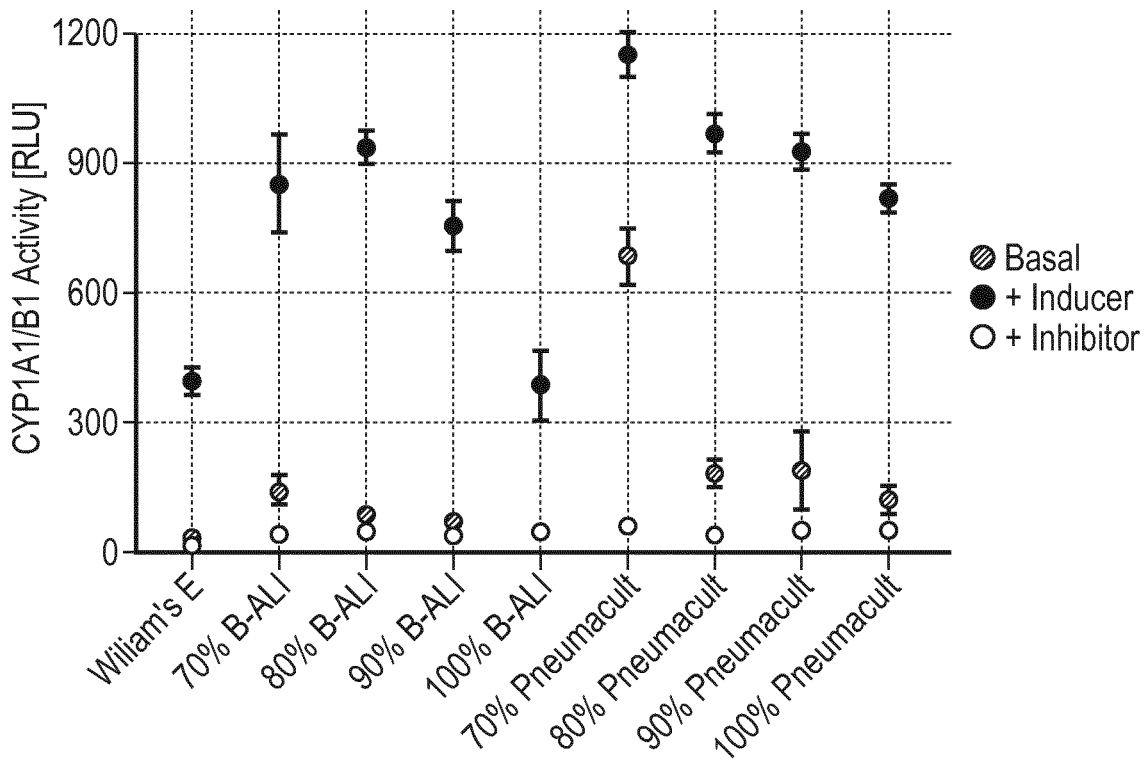

Fold regulation of the expression of phase 1 drug metabolism enzyme-encoding genes in 3-dimensional organotypic lung cultures is assessed at 1, 2, 3, and 4 weeks. Gene expression is compared between lung cultures treated with TCDD and rifampicin for 48 hours (n=3) and untreated cultures (n=3), and fold changes are calculated. All of the genes shown in FIG. 7 are upregulated at week 3 in the presence of TCDD and rifampicin. All of the genes shown in FIG. 7 are downregulated at week 4 in the presence of TCDD and rifampicin.

Example 21

Plates Used to Create Lung Spheroids

The plates used to form the spheroids are named Corning® spheroids microplate (Corning®, ref. 4520). The cells used to prepare the spheroids (HepaRG) are thawed and immediately seeded into these plates. Since the wells are coated with an ultra-low adhesion surface, the cells do not attach and instead aggregate. After a week, the cells form a spheroid that can be further used for the experiments. CYP induction (a metabolic marker), albumin secretion (a metabolic and health marker) and ATP content (a marker of health) are all increased meaning that the spheroids are healthier in these wells as compared to wells from InSphero. Without being bound by any theory, this may be due to the increased volume of culture medium that can be contained in the Corning® spheroids microplate. The secretion of alpha GST is strongly reduced using the Corning® plates compared to InSphero.

CYP inducibility is maintained for two more weeks (with InSphero CYP inducibility is only maintained for 2 weeks while it is maintained for 4 weeks with Corning®). The ATP content is found to be 30% higher during the first 3 weeks and 40% higher at week 4. Albumin secretion is also higher at week 2 (10% higher) and week 3 (20%) but it and then reaches similar values to the InSphero plates. For the alpha GST release, a large difference is seen at week 4 (50% decrease) and week 5 (63% decrease).

Example 22

Summary of Results

In this study, 3-dimensional organotypic cultures of the lung and liver with respect to health, morphology and metabolic activity over a 4-week period are studied. The results show that: 3-dimensional bronchial cultures maintained at the air-liquid interface have a stable ATP content up until week 3 and exhibit no morphological changes over the test period. They retain the ability to produce ATP in response to stimulation during the 4-week period. In addition, 3-dimensional bronchial cultures exhibit higher CYP1A1/B1 activity at weeks 2 and 3, while expression of several (but not all) metabolic enzyme-encoding genes is elevated following induction throughout the test period (see FIG. 7). HepaRG spheroids have a stable morphology, albeit with a decrease in ATP content and CYP1A1 and 1A2 inducibility and a minimal increase in α-GST release over the test period. Unexpectedly, albumin secretion decreases rapidly after the first week of culture.

Maintaining the spheroids for 9 days with Complete William's E medium and Complete Pneumacult-ALI medium mixtures, ATP content, cytochrome P450 1A1 and cytochrome P450 B1 inducibility and secreted albumin are all improved compared to Complete William's E medium condition. At the same time, the number of necrotic or apoptotic cells and the GSH/GSSG ratio are negatively affected by the mixtures which may be a result of oxidative stress. Tests performed with Complete William's E medium and Complete B-ALI medium mixtures also show an increase in ATP content, cytochrome P450 1A1 and cytochrome P450 B1 inducibility and secreted albumin compared to Complete William's E medium. Using Complete Pneumacult-ALI medium for co-cultures is suitable in certain embodiments of the present disclosure. As one aspect of the disclosure relates to a two organs on a chip system with interconnected lung and liver tissues, the use of 100% Complete Pneumacult-ALI medium allows the use of lung cultures without any further optimisation. As the liver spheroids appear to be maintainable with 100% Complete Pneumacult-ALI medium, it is a suitable condition for co-culture in the multi-organ-on-a-chip system.

Any publication cited or described herein provides relevant information disclosed prior to the filing date of the present application. Statements herein are not to be construed as an admission that the inventors are not entitled to antedate such disclosures. All publications mentioned in the above specification are herein incorporated by reference. Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in cellular and molecular biology or related fields are intended to be within the scope of the following claims.

TABLE 1

Comparison of the results obtained in each culture medium. The fold change is expressed as compared to William's E medium alone.

|  | 70% P | 80% P | 90% P | 100% P | 70% B | 80% B | 90% B | 100% B |
|---|---|---|---|---|---|---|---|---|
| CYP induction | 2.9 | 2.5 | 2.3 | 2.1 | 2.1 | 2.4 | 1.9 | 1.0 |
| ATP content | 2.6 | 2.7 | 2.9 | 2.7 | 2.1 | 2.4 | 2.1 | 1.5 |
| Albumin | 2.5 | 3.1 | 2.6 | 3.3 | 2.0 | 2.1 | 1.8 | 1.9 |

B = Complete B-ALI ™ medium at 70%, 80%, 90% and 100% (v/v). At 70%, 80% and 90% (v/v) the remaining volume is made up to 100% (v/v) with William's E medium.
P = Complete PneumaCult-ALI medium at 70%, 80%, 90% and 100% (v/v). At 70%, 80% and 90% (v/v) the remaining volume is made up to 100% (v/v) with William's E medium.

TABLE 2

Composition of William's E medium

| Components | Molecular Weight | Concentration (mg/L) | mM |
|---|---|---|---|
| Amino Acids | | | |
| Glycine | 75.0 | 50.0 | 0.6666667 |
| L-Alanine | 89.0 | 90.0 | 1.011236 |
| L-Arginine | 174.0 | 50.0 | 0.28735632 |
| L-Asparagine-H2O | 150.0 | 20.0 | 0.13333334 |
| L-Aspartic acid | 133.0 | 30.0 | 0.22556391 |
| L-Cysteine | 121.0 | 40.0 | 0.3305785 |
| L-Cysteine 2HCl | 313.0 | 26.07 | 0.08329073 |
| L-Glutamic Acid | 147.0 | 50.0 | 0.34013605 |
| L-Histidine | 155.0 | 15.0 | 0.09677419 |
| L-Isoleucine | 131.0 | 50.0 | 0.3816794 |
| L-Leucine | 131.0 | 75.0 | 0.57251906 |
| L-Lysine hydrochloride | 183.0 | 87.46 | 0.47792348 |
| L-Methionine | 149.0 | 15.0 | 0.10067114 |
| L-Phenylalanine | 165.0 | 25.0 | 0.15151516 |

TABLE 2-continued

Composition of William's E medium

| Components | Molecular Weight | Concentration (mg/L) | mM |
|---|---|---|---|
| L-Proline | 115.0 | 30.0 | 0.26086956 |
| L-Serine | 105.0 | 10.0 | 0.0952381 |
| L-Threonine | 119.0 | 40.0 | 0.33613446 |
| L-Tryptophan | 204.0 | 10.0 | 0.04901961 |
| L-Tyrosine disodium salt dihydrate | 261.0 | 50.65 | 0.19406131 |
| L-Valine | 117.0 | 50.0 | 0.42735043 |
| Vitamins | | | |
| Ascorbic Acid | 176.0 | 2.0 | 0.011363637 |
| Biotin | 244.0 | 0.5 | 0.0020491802 |
| Choline chloride | 140.0 | 1.5 | 0.010714286 |
| D-Calcium pantothenate | 477.0 | 1.0 | 0.002096436 |
| Ergocalciferol | 397.0 | 0.1 | 2.5188917E-4 |
| Folic acid | 441.0 | 1.0 | 0.0022675737 |
| Menadione sodium bisulfate | 276.0 | 0.01 | 3.6231882E-5 |
| Niacinamide | 122.0 | 1.0 | 0.008196721 |
| Pyridoxal hydrochloride | 204.0 | 1.0 | 0.004901961 |
| Riboflavin | 376.0 | 0.1 | 2.6595744E-4 |
| Thiamine hydrochloride | 337.0 | 1.0 | 0.002967359 |
| Vitamin A (acetate) | 328.0 | 0.1 | 3.0487805E-4 |
| Vitamin B12 | 1355.0 | 0.2 | 1.4760147E-4 |
| alpha Tocopherol phos. Na salt | 554.7 | 0.01 | 1.8027762E-5 |
| i-Inositol | 180.0 | 2.0 | 0.011111111 |
| Inorganic Salts | | | |
| Calcium Chloride (CaCl2) (anhyd. ) | 111.0 | 200.0 | 1.8018018 |
| Cupric sulfate (CuSO4-5H2O) | 250.0 | 1.0E-4 | 3.9999998E-7 |
| Ferric nitrate (Fe(NO3)-9H2O) | 404.0 | 1.0E-4 | 2.4752475E-7 |
| Magnesium Sulfate (MgSO4) (anhyd. ) | 120.0 | 97.67 | 0.8139166 |
| Manganese chloride (MnCl2-4H2O) | 198.0 | 1.0E-4 | 5.050505E-7 |
| Potassium Chloride (KCl) | 75.0 | 400.0 | 5.3333335 |
| Sodium Bicarbonate (NaHCO3) | 84.0 | 2200.0 | 26.190475 |
| Sodium Chloride (NaCl) | 58.0 | 6800.0 | 117.24138 |
| Sodium Phosphate monobasic (NaH2PO4) anhydrous | 138.0 | 140.0 | 1.0144928 |
| Zinc sulfate (ZnSO4-7H2O) | 288.0 | 2.0E-4 | 6.9444445E-7 |
| Other Components | | | |
| D-Glucose (Dextrose) | 180.0 | 2000.0 | 11.111111 |
| Glutathione (reduced) | 307.0 | 0.05 | 1.6286645E-4 |
| Methyl linoleate | 295.0 | 0.03 | 1.0169491E-4 |
| Phenol Red | 376.4 | 10.0 | 0.026567481 |
| Sodium Pyruvate | 110.0 | 25.0 | 0.22727273 |

The invention claimed is:

1. A cell culture comprising a 3-dimensional liver spheroid and a medium comprising a mixture of Complete B-ALI medium and Complete William's E medium, the mixture comprising from 75% to 95% by volume Complete B-ALI Medium with the remaining volume being made up of Complete William's E medium.

2. A 3-dimensional multi-organ culture system comprising a 3-dimensional liver spheroid and a 3-dimensional-lung epithelial spheroid in a culture medium, said culture medium selected from the group consisting of a culture medium comprising or consisting or consisting essentially of a mixture of Complete B-ALI medium and Complete William's E medium, the mixture comprising from 70% to 95% by volume Complete B-ALI Medium with the remaining volume being made up of Complete William's E medium.

3. A method comprising culturing a 3-dimensional liver spheroid, or co-culturing a 3-dimensional liver spheroid and a 3-dimensional lung epithelial spheroid in a medium comprising a mixture of Complete B-ALI medium and Complete William's E medium, the mixture comprising from 70% to 95% by volume Complete B-ALI Medium with the remaining volume being made up of Complete William's E medium.

* * * * *